(12) United States Patent
Shoemaker et al.

(10) Patent No.: US 10,111,907 B2
(45) Date of Patent: *Oct. 30, 2018

(54) METHODS OF TREATING ISCHEMIA

(71) Applicant: FATE THERAPEUTICS, INC., San Diego, CA (US)

(72) Inventors: Dan Shoemaker, San Diego, CA (US); Pratik S. Multani, San Diego, CA (US); John D. Mendlein, Encinitas, CA (US); David Robbins, Temecula, CA (US)

(73) Assignee: Fate Therapeutics, Inc., San Diego, CA (US)

( * ) Notice: Subject to any disclaimer, the term of this patent is extended or adjusted under 35 U.S.C. 154(b) by 1126 days.

This patent is subject to a terminal disclaimer.

(21) Appl. No.: 14/362,385

(22) PCT Filed: Nov. 29, 2012

(86) PCT No.: PCT/US2012/066984
§ 371 (c)(1),
(2) Date: Jun. 2, 2014

(87) PCT Pub. No.: WO2013/082241
PCT Pub. Date: Jun. 6, 2013

(65) Prior Publication Data
US 2014/0348802 A1    Nov. 27, 2014

Related U.S. Application Data

(60) Provisional application No. 61/566,494, filed on Dec. 2, 2011.

(51) Int. Cl.
| | | |
|---|---|---|
| *A61K 35/28* | (2015.01) | |
| *A61K 31/5575* | (2006.01) | |
| *A61K 31/573* | (2006.01) | |
| *C12N 5/0789* | (2010.01) | |
| *A61K 35/12* | (2015.01) | |

(52) U.S. Cl.
CPC .......... *A61K 35/28* (2013.01); *A61K 31/5575* (2013.01); *A61K 31/573* (2013.01); *C12N 5/0647* (2013.01); *A61K 2035/124* (2013.01); *C12N 2501/02* (2013.01); *C12N 2501/39* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,077,049 A | 12/1991 | Dunn et al. |
| 5,397,706 A | 3/1995 | Correa et al. |
| 5,442,033 A | 8/1995 | Bezwada |
| 5,460,964 A | 10/1995 | McGlave et al. |
| 5,635,387 A | 6/1997 | Fei et al. |
| 5,648,331 A | 7/1997 | Koudsi et al. |
| 5,677,136 A | 10/1997 | Simmons et al. |
| 5,716,827 A | 2/1998 | Tsukamoto et al. |
| 5,750,397 A | 5/1998 | Tsukamoto et al. |
| 5,753,516 A | 5/1998 | Heagy et al. |
| 5,759,793 A | 6/1998 | Schwartz et al. |
| 5,854,033 A | 12/1998 | Lizardi |
| 5,945,337 A | 8/1999 | Brown |
| 6,191,109 B1 | 2/2001 | Besner et al. |
| 6,207,802 B1 | 3/2001 | Zsebo et al. |
| 6,610,719 B2 | 8/2003 | Paralkar et al. |
| 6,747,037 B1 | 6/2004 | Old et al. |
| 6,891,062 B2 | 5/2005 | Oida et al. |
| 7,131,958 B2 | 11/2006 | Deverre |
| 7,147,626 B2 | 12/2006 | Goodman et al. |
| 7,625,752 B2 | 12/2009 | Casper et al. |
| 8,551,782 B2 | 10/2013 | Zon et al. |
| 8,563,310 B2 | 10/2013 | Zon et al. |
| 9,107,909 B2 * | 8/2015 | Pelus ............. A61K 31/00 |
| 9,675,641 B2 * | 6/2017 | Pelus ............. A61K 35/14 |
| 2002/0115586 A1 | 8/2002 | Enikolopov et al. |
| 2003/0022363 A1 | 1/2003 | Rao et al. |
| 2005/0054103 A1 | 3/2005 | Peled et al. |
| 2005/0074435 A1 | 4/2005 | Casper et al. |
| 2005/0101599 A1 | 5/2005 | Zeiher et al. |
| 2006/0005153 A1 | 1/2006 | Maruyama et al. |

(Continued)

FOREIGN PATENT DOCUMENTS

| | | |
|---|---|---|
| CA | 2743255 | 6/2010 |
| EP | 1563846 | 8/2005 |

(Continued)

OTHER PUBLICATIONS

Adams et al., "Haematopoietic stem cells depend on $G\alpha_s$-mediated signalling to engraft bone marrow," Nature, 459:103-107 (2009).
Attar et al., "Regulation of hematopoietic stem cell growth," Leukemia 18:1760-1768 (2004).
Barany, "Genetic disease detection and DNA amplification using cloned thermostable ligase," Proc. Natl. Acad. Sci. USA, 88(1):189-193 (1991).
Barker et al., "Mining the Wnt pathway for cancer therapeutics," Nat. Rev. Drug Discov., 5:997-1014 (2006).
Brandt et al., "Practical aspects of preparative HPLC in pharmaceutical and development production," LC-GC Europe, pp. 2-5 (2002).

(Continued)

*Primary Examiner* — Blaine Lankford
(74) *Attorney, Agent, or Firm* — Jones Day

(57) ABSTRACT

The invention provides compositions comprising stem and/or progenitor cells that have been treated to enhance the therapeutic properties of the cells for treating ischemia. In particular, the present invention relates to the use of stem and/or progenitor cells having enhanced therapeutic properties to treat an ischemic tissue, a tissue damaged by ischemia, or at least one symptom associated with an ischemic tissue or a tissue damaged by ischemia.

12 Claims, 5 Drawing Sheets

(56) References Cited

U.S. PATENT DOCUMENTS

| | | |
|---|---|---|
| 2006/0121085 A1 | 6/2006 | Warren et al. |
| 2006/0247214 A1 | 11/2006 | DeLong et al. |
| 2007/0154563 A1 | 7/2007 | Behnam et al. |
| 2009/0029912 A1 | 1/2009 | Gronthos et al. |
| 2009/0220465 A1 | 9/2009 | Scadden et al. |
| 2010/0143317 A1 | 6/2010 | Pecora et al. |
| 2010/0322907 A1 | 12/2010 | Calvi et al. |
| 2012/0189594 A1 | 7/2012 | Zon et al. |
| 2012/0202288 A1 | 8/2012 | Mendlein et al. |
| 2013/0209423 A1 | 8/2013 | Zon et al. |
| 2013/0209424 A1 | 8/2013 | Zon et al. |
| 2013/0216507 A1 | 8/2013 | Zon et al. |
| 2014/0369972 A1 | 12/2014 | Shoemaker et al. |

FOREIGN PATENT DOCUMENTS

| | | |
|---|---|---|
| JP | 2009530408 | 8/2009 |
| RU | 2002113565 | 11/2000 |
| WO | WO 95/06112 | 3/1995 |
| WO | WO 96/40866 | 12/1996 |
| WO | WO 00/38663 | 7/2000 |
| WO | WO 00/50568 | 8/2000 |
| WO | WO 01/12596 | 2/2001 |
| WO | WO 2004/032965 | 4/2004 |
| WO | WO 2004/078169 | 9/2004 |
| WO | WO 2006/047476 | 5/2006 |
| WO | WO 2006/078886 | 7/2006 |
| WO | WO 2006/086639 | 8/2006 |
| WO | WO 2007/070964 | 6/2007 |
| WO | WO 2007/071456 | 6/2007 |
| WO | WO 2007/112084 | 10/2007 |
| WO | WO 2008/021475 | 2/2008 |
| WO | WO 2008/056963 | 5/2008 |
| WO | WO 2008/073748 | 6/2008 |
| WO | WO 2009/104807 | 8/2009 |
| WO | WO 2009/134532 | 11/2009 |
| WO | WO 2010/036537 A2 | 4/2010 |
| WO | WO 2010/054271 | 5/2010 |
| WO | WO 2010/108028 | 9/2010 |
| WO | WO 2011/060381 | 5/2011 |
| WO | WO 2012/021845 | 2/2012 |
| WO | WO 2013/082241 | 6/2013 |
| WO | WO 2013/082243 | 6/2013 |

OTHER PUBLICATIONS

Bug et al., "Valproic Acid Stimulates Proliferation and Self-renewal of Hematopoietic stem cells," Cancer Res., 65(7):2537-2541 (2005).
Capmany et al., "Short-term, serum-free, static culture of cord blood-derived CD34+ cells: effects of FLT3-L and MIP-1α on in vitro expansion of hematopoietic progenitor cells," Haematologica, 84:675-682 (1999).
Cayman Chemical Company, "16, 16-dimethyl Prostaglandin E2. Catalog No. 14750, CAS Registry No. 39746-25-3," Product Information, Mar. 30, 2006, one page.
Chen et al., "Intravenous administration of human umbilical cord blood reduces behavioral deficits after stroke in rats", Stroke, 32(11):2682-2688 (2001).
Cohn et al., "Crypt stem cell surivival in the mouse intestinal epithelium is regulated by prostaglandins synthesized through cyclooxygenase-1," J. Clin. Invest., 99(6):1367-1379 (1997).
Crawford, "Thoracoabdominal aortic aneurysms: Preoperative and intraoperative factors determining immediate and long-term results of operations in 605 patients," Vas. Surg. 3:389-404 (1986).
Curnow et al., "Topical Glucocorticoid Therapy Directly Induces Up-Regulation of Functional CXCR4 on Primed T Lymphocytes in the Aqueous Humor of Patients with Uveitis," J. Immunol., 172:7154-7161 (2004).
Daley et al., "Ex vivo expansion of human hematopoietic progenitor cells in serum-free StemProTM-34 Medium," Focus 18(3):62-67 (1996).
Davidson and Zon, "The 'definitive' (and 'primitive') guide to zebrafish hematopoiesis," Oncogene, 23:7233-7246, (2004).
De Jong and Zon, "Use of the zebrafish system to study primitive and definitive hematopoiesis," Annu. Rev. Genet., 39:481-501, (2005).
Desplat et al., "Is the COX-2 effect on accelerated hematopoiesis mediated by prostaglandin E2?" Exp. Hematol., 28:741-742, (2000).
Dupuis et al., "Prostaglandin $E_2$ stimulates the growth of human blood CD34+progenitors," Prostaglandins & Other Lipid Mediators, 55:179-186 (1998).
FDA +Sterile drug products produced by aseptic processing draft, 50 pages, Sep. 22, 2002.
FDA Guidance for Industry, Sterile drug products produced by aseptic processing—current good manufacturing practice, 63 pages (2003).
Fehér et al., "Prostagladin $E_2$ as stimulator of haemopoietic stem cell proliferation," Nature, 247:550-551 (1974).
Freedman et al., "Autocrine and paracrine growth control by granulocyte-monocyte colony-stimulating factor of acute lymphoblastic leukemia cells," Blood, 81(11):3068-3075 (1993).
Galloway et al, "Ontogeny of hematopoiesis: examining the emergence of hematopoietic cells in the vertebrate embryo," Curr. Top. Dev. Biol., 53:139-158 (2003).
Gentile et al., "In vivo modulation of murine myelopoiesis following intravenous administration of prostaglandin E2," Blood, 62(5):1100-1107 (1983).
Gidali et al., "The effect of E type prostaglandins on the proliferation of haemopoietic stem cells in vivo," Cell Tissue Kinet., 10:365-373 (1977).
Goessling et al., "Genetic interaction of PGE2 and Wnt signaling regulates developmental specification of stem cells and regeneration," Cell, vol. 136, Supplemental Data (2009).
Goessling et al., "Genetic interaction of PGE2 and Wnt signaling regulates developmental specification of stem cells and regeneration," Cell, 136:1136-1147 (2009).
Goessling et al., "Prostaglandin E2 enhances human cord blood stem cell xenotransplants and shows long-term safety in preclinical nonhuman primate transplant models," Cell Stem Cell, 8(4):445-458 (2011).
Goichberg et al., "cAMP-induced PKCzeta activation increases functional CXCR4 expression on human CD34+ hematopoietic progenitors," Blood, 107(3):870-879 (2006).
Guatelli et al., "Isothermal, in vitro amplification of nucleic acids by a multienzyme reaction modeled after retroviral replication," Proc. Natl. Acad. Sci USA, 87(5):1874-1878 (1990).
Hanson et al., "16, 16-Dimethyl prostaglandin e2 induces radioprotection in murine intestinal and hematopoietic stem cells," Radiat. Res., 103:196-203 (1985).
Herrler et al., Prostaglandin E positively modulates endothelial progenitor cell homeostasis: an advanced treatment modality for autologous cell therapy, J. Vasc. Res., 46:333-346 (2009).
Hoggatt et al., "Eicosanoid regulation of hematopoiesis and hematopoietic stem and progenitor trafficking," Leukemia, 24(12):1993-2002 (2010).
Hoggatt et al., "Prostaglandin E2 enhances hematopoietic stem cell homing, survival, and proliferation," Blood, 113(22):5444-5455 (2009).
Horowitz, "Uses and Growth of Hematopoietic Cell Transplantation," In: Blume KG, Forman SJ, Appelbaum FR, eds. Thomas' Hematopoietic Cell Transplantation, 3rd ed. Malden, Mass: Blackwell, pp. 9-15 (2007).
Hsia and Zon, "Transcriptional regulation of hematopoietic stem cell development in zebrafish," Exp. Hematol., 33:1007-1014 (2005).
Hubbell et al., Principles of Tissue Engineering, $2^{nd}$ Ed, Academic Press, San Diego, CA, pp. 237-250 (2000).
Jandl, Blood: Textbook of Hematology, $2^{nd}$ Ed., Little, Brown and Company, Boston, MA pp. 544-545 (1996).
Janssens et al., "The Wnt-dependent signaling pathways as target in oncology drug discovery," Invest. New Drugs, 24:263-280 (2006).
Kahn et al., "Overexpression of CXCR4 on human CD34+ progenitors increases their proliferation, migration, and NOD/SCID repopulation," Blood, 103(8):2942-2949 (2004).
Kamel et al., "Potential interaction of prostaglandin and Wnt signaling pathways mediating bone cell responses to fluid flow," J. Bone and Mineral Res., vol. 21, NR, Suppl. 1, p. S92, (2006).

(56) References Cited

OTHER PUBLICATIONS

Kataoka et al., "Prostaglandin E2 receptor EP4 agonist induces Bcl-xL and independently activates proliferation signals in mouse primary hepatocytes," J. Gastroenterology, 40(6):610-616 (2005).
Kishi et al., "Bone marrow suppression induced by high dose valproic acid," Arch. Dis. Child., 71(2):153-155 (1994).
Kollet et al., "Human CD34+CXCR4⁻ sorted cells harbor intracellular CXCR4, which can be functionally expressed and provide NOD/SCID repopulation," Blood, 100(8):2778-2786 (2002).
Konturek et al., "Prostaglandins and ulcer healing," J. Physiology Pharmacology 56 (Supp 5):5-31 (2005).
Kouchoukos et al., "Elective hypothermic cardiopulmonary bypass and circulatory arrest for spinal cord protection during operations on the thoracoabdominal aorta, " J. Thorac. Cardiovasc. Surg., 99:659-664 (1990).
Krishnan et al., "Regulation of bone mass by Wnt signaling," J. Clin. Invest., 116(5):1202-1209 (2006).
Kurtzberg et al., "Unrelated placental blood in marrow transplantation," Stem Cells 18:153-154 (2000).
Kwoh et al., "Transcription-based amplification system and detection of amplified human immunodeficiency virus type 1 with a bead-based sandwich hybridization format," Proc. Natl. Acad. Sci USA, 86(4):1173-1177 (1989).
Kyriakou et al., "Factors that influence short-term homing of human bone marrow-derived mesenchymal stem cells in a xenogeneic animal model," Haematologica—The Hematology Journal 93(10):1457-1465 (2008).
Lee et al., "Mechanisms involved in prostaglandin E2-mediated neuroprotection against TNF-alpha: possible involvement of multiple signal transduction and beta-catenin/T-Cell factor," J. Neuroimmunol., 155(1-2):21-31 (2004).
Liu et al., "Ex vivo expansion of hematopoietic stem cells derived from umbilical cord blood in rotating wall vessel," J. Biotechnol., 124:592-601 (2006).
Lizardi et al., "Exponential amplification of recombinant-RNA hybrization probes," Bio/Technology, 6:1197 (1988).
McCowage et al., "Multiparameter-fluorescence activated cell sorting analysis of retroviral vector gene transfer into primitive umbilical cord blood cells," Exp. Hematol., 26(4):288-298 (1998).
North and Zon, "Modeling human hematopoietic and cardiovascular diseases in zebrafish," Dev. Dyn., 228:568-583 (2003).
North et al., "Prostaglandin E2 regulates vertebrate haematopoietic stem cell homeostasis," Nature, 447:1007-1011 (2007).
Okamoto et al., "Molecular and clinical basis for the regeneration of human gastrointestinal epithelia," J. Gastroenterol, 39:1-6 (2004).
Okunieff et al., "Effects of hydralazine on in vivo tumor energy metabolism, hematopoietic radiation sensitivity, and cardiovascular parameters," Int. J. Radiat. Oncol. Biol. Phys., 16(5):1145-1148 (1989).
Pachence et al., Principles of Tissue Engineering, $2^{nd}$ Ed, Academic Press, San Diego, CA pp. 263-278 (2000).
Paladin Labs Inc., "Summary basis of decision (SBD)$^{PR}$VANTAS® Histrelin acetate subdermal implant, 50mg," Submission Control No. 092567, 24 pages (2006).
Pelus et al., "Pleiotropic effects of prostaglandin $E_2$ in hematopoiesis; prostaglandin $E_2$ and other eicosanoids regulate hematopoietic stem and progenitor cell function," Prostaglandins & other Lipid Mediators, 96:3-9 (2011).
Quackenbush, "Microarray data normalization and transformation," Nat. Genet., 32(Suppl):496-501 (2002).

SAFC Biosciences, Technical Bulletin, BIOEZE™ Bags—polyethylene (PE) film, 4 pages (2006).
Saltzman et al., Principles of Tissue Engineering, $2^{nd}$ Ed, Academic Press, San Diego, CA pp. 221-236 (2000).
Sankaranarayanan et al., "Radioprotective Effects of Prostaglandins for Chromosomal Aberrations and Cell Killing in V79 Chinese Hamster Cells Grown as Spheroids in Vitro and for Mouse Spermatogonial Stem Cells and Bone Marrow Cells in Vivo, " Int. J. Radiation Biol., 67(1):47-55 (1995).
Schena et al., "Quantitative monitoring of gene expression patterns with a complementary DNA microarray," Science, 270(5235):467-470 (1995).
Schmidt et al., "Influence of prostaglandin on repair of rat stomach damaged by absolute ethanol," J. Surg. Res., 41(4):367-377 (1986).
Shao et al., "Prostaglandin E2 induces VEGF expression via the Wnt pathway," Gastroenterology, vol. 128, NR. 4, Suppl. 2, p. A146 (2005).
Shetsov et al., "Activation of beta-catenin signaling pathways by classical G-protein-coupled receptors: mechanisms and consequences in cycling and non-cycling cells," Cell Cycle, 5(20):2295-2300(2006) Epub Oct. 16, 2006.
Shi et al., "Regulation of CXCR4 expression in human mesenchymal stem cells by cytokine treatment: role in homing efficiency in NOD/SCID mice," Haematologica—The Hematology Journal 92(7):897-904 (2007).
Stier et al., "Notch 1 activation increases hematopoietic stem cell self-renewal in vivo and favors lymphoid over myeloid lineage outcome, " Blood, 99(7):2369-78 (2002).
Takayama et al., Principles of Tissue Engineering, $2^{nd}$ Ed, Academic Press, San Diego, CA pp. 209-220 (2000).
Thomson et al., Principles of Tissue Engineering, $2^{nd}$ Ed, Academic Press, San Diego, CA pp. 251-262 (2000).
Tocris Bioscience, Safety Data Sheet. Product Name: Prostaglandin E2. Catalog No. 2296. CAS No. 363-24-6, Version 2.0 SDS Revision Date: Dec. 19, 2008, SDS Print Date Jan. 22, 2014, four pages.
Tseng Al-Sun et al., "The GSK-3 inhibitor BIO promotes proliferation in mammalian," Chem. Biol., 13:957-963 (2006).
Urakawa et al., "Study of 16, 16-dimethyl prostaglandin E2 for prevention of stress ulcer after hepatectomy of experimental cirrhotic liver and its influence on hepatic regeneration," Database EMBASE [online]1990.
Wagner et al., "Transplantation of unrelated donor umbilical cord blood in 102 patients with malignant and nonmalignant diseases: influence of CD34 cell dose and HLA disparity on treatment-related mortality and survival," Blood, 100(5):1611-1618 (2002).
Walden, TL Jr. et al., Abstract only. "16,16-Dimethyl prostaglandin E2 increases survival in mice following irradiation," Radial. Res., 109(3):440-448 (1987).
Weis et al., "Detection of rare mRNAs via quantitative RT-PCT," Trends Genet., 8(8):263-264 (1992).
WHO Pharmacopoeia Library, "Methods of analysis: 1. physical and physiochemical methods: 1.14 chromatography: 1.14.4 high-performance liquid chromatography," Retrieved from internet. http://apps.who.int/phint/en/p/docf/, Aug. 15, 2003.
Wu et al., "Extracellular calcium increases CXCR4 expression on bone marrow-derived cells and enhances pro-angiogenesis therapy," J. Cell. Mol. Med., 13(9B):3764-3773 (2009).
Cutler et al., "Ex Vivo Treatment of Hematopoietic Stem Cells With 16,16-Dimethyl Prostaglandin E2 (FT1050) Improves Engraftment and Hematopoietic Reconstitution," *Biol. Blood Marrow Transplant.*, 17(2):S226 (2011).

\* cited by examiner

METHODS OF TREATING ISCHEMIA

CROSS-REFERENCE TO RELATED APPLICATIONS

This application is 371 of PCT/US2012/066984, filed Nov. 29, 2012, which application claims the benefit under 35 U.S.C § 119(e) of U.S. Provisional Application No. 61/566,494, filed Dec. 2, 2011, each of which is incorporated herein by reference in its entirety.

BACKGROUND

Technical Field

The present invention relates generally to compositions and methods for treating ischemia. In particular, the present invention relates to the use of stem and/or progenitor cells having enhanced therapeutic properties to treat an ischemic tissue and/or the resulting ischemic tissue damage.

Description of the Related Art

The viability of cells, tissues, and organs in the human body depends on adequate blood flow. Adequate blood flow provides cells with oxygen, glucose, and much needed nutrients that are important for the regulation of cellular physiology and metabolism. Adequate blood flow also allows cell and tissues to respond appropriately to environmental conditions that pose a risk of tissue damage or stress.

Disruption of blood flow to tissues and organs is known as ischemia. Ischemia can be acute or chronic. Both acute and chronic forms of ischemia result in the loss of adequate nutrients to the cells, and if prolonged, will result in hypoxic and/or anoxic conditions. If the ischemia is left untreated, the cells may undergo necrosis or apoptosis, thereby jeopardizing the integrity and health of the tissue or organ.

Ischemia affects millions of patients in the United States each year. Ischemia is caused by a virtually limitless variety of genetic conditions, environmental insults, traumatic injury, or surgical interventions. The most common types of ischemia patients suffer from include, but are not limited to cerebral ischemias, spinal cord injuries, cardiovascular ischemias, limb ischemias, intestinal ischemias, renal ischemias, dermal ischemias (e.g., burns and frostbite wounds) and ischemias resulting from medical and surgical procedures, including, but not limited to organ transplants, and skin grafts.

Cerebral ischemia, referred to as stroke, is the third leading cause of death and the leading cause of serious, long-term disability in the United States (U.S. Centers for Disease Control and Prevention). More than 140,000 people die each year from stroke in the United States. Id. Each year, approximately 795,000 people suffer a stroke. Id. About 600,000 of these are first attacks, and 185,000 are recurrent attacks. Id. Stroke is the interruption or reduction of blood flow in the arteries feeding the brain. When deprived of blood, and thus, oxygen and glucose, brain tissue may undergo ischemic necrosis or infarction. The metabolic events thought to underlie such cell degeneration and death include: energy failure through ATP depletion; cellular acidosis; glutamate release; calcium ion influx; stimulation of membrane phospholipid degradation and subsequent free-fatty-acid accumulation; and free radical generation.

Heart attacks and angina result in myocardial ischemia. 1.5 million heart attacks occur in the United States each year. Id. Almost 14 million Americans have a history of heart attack or angina. Id. More than 500,000 deaths annually can be attributed to heart attacks. Id. A heart attack occurs about every 20 seconds with a heart attack death about every minute. Id. Costs related to heart attack exceed 60 billion dollars per year. Id. Myocardial ischemia occurs when the heart muscle does not receive an adequate blood supply and is thus deprived of necessary levels of oxygen, glucose, and nutrients, resulting in angina, and in many instances, infarction (necrosis) of the myocardial muscle.

Another common cause of myocardial ischemia is atherosclerosis, which is the progressive buildup of plaque—fatty deposits and other cells—in the walls of your arteries that causes blockages in the blood vessels (coronary arteries) that provide blood flow to the heart muscle. Before turning 35, two out of three Americans will have some degree of plaque build-up in their arteries. Heart Disease and Stroke Statistics: 2009 Update. American Heart Association. Jan. 13, 2009. Atherosclerosis is usually a slow and progressive condition that often causes coronary heart disease (CHD)—the leading cause of death in the United States. The total estimated direct and indirect cost of coronary heart disease and stroke in 2009 is $234.3 billion. Id.

Spinal cord injury is the most serious complication of spinal column trauma and also of operations on the aorta for treatment of thoracic and thoracoabdominal aneurysms (Kouchoukos. *Thorac. Cardiovasc. Surg.* 99:659-664, (1990)). As described in U.S. Pat. No. 5,648,331, the spinal cord is the organ most sensitive to ischemia during cross-clamping of the aorta, where the resultant injury may produce paraparesis or paraplegia. Spinal cord ischemia and paraplegia develop in approximately eleven percent (11%) of patients undergoing elective descending thoracic and thoracoabdominal aneurysm repair and nearly forty percent (40%) undergoing emergent repairs (Crawford. *Vas. Surg.* 3:389-402, (1986)).

Ischemic events affecting the intestines play a major role of the mortality and morbidity or numerous patients. As described in U.S. Pat. No. 6,191,109, ischemic injury to the small intestine leads to mucosol destruction, bacterial translocation and perforation. The mesenteric arteries supply blood to your small and large intestines. Ischemia occurs when your blood cannot flow through your arteries and your intestines do not receive the necessary oxygen for digestion. Mesenteric ischemia can be acute or chronic and usually involves the small intestine. If left untreated, blockage of the mesenteric arteries may worsen and cause tissues in your intestine to die because they lack enough blood flow.

Critical Limb Ischemia or CLI results from severe obstruction of the arteries, inadequate blood flow or arterial occlusive disease, which seriously decreases blood flow to the extremities (hands, feet and legs) and has progressed to the point of severe pain and even skin ulcers or sores. CLI differs from acute limb ischemia, which generally follows arterial thrombosis or peripheral thromboembolism. Patients with CLI often suffer from severe pain caused by ischemia, tissue loss, ischemic neuropathy, or a combination of these factors. If left untreated, ischemia limbs may become gangrenous and require amputation.

Dermal ischemia results from lack of adequate blood flow to the dermis, and is most often the result of wounding, burns, or frostbite. In burn wounds, the surface tissue necrosis of the initial burn eschar is caused mainly by the heat or chemical insult and is essentially irreversible. Deep and peripheral to the surface tissue necrosis, there is a sizable area of ischemic tissue injury where cells are viable but can easily be further damaged, if left untreated. The area peripheral to and below the ischemic zone is characterized by minimal cell injury but with vasodilatation due to neighboring inflammation-induced mediators is still at risk for ischemia.

Frostbite, once almost exclusively a military problem, is becoming more prevalent among the general population. Research into the pathophysiology has revealed marked similarities in inflammatory processes to those seen in thermal burns and ischemia/reperfusion injury. Although the surgical management of frostbite involves delayed debridement 1 to 3 months after demarcation, recent improvements in radiologic assessment of tissue viability have led to the possibility of earlier surgical intervention. In addition, several adjunctive therapies, including vasodilators, thrombolysis, hyperbaric oxygen, and sympathectomy, are possible.

Currently, resolution of acute and chronic ischemia requires restoration of tissue perfusion and blood flow often using surgical means, which further places patients as risk for ischemic tissue damage. Restoration of blood flow after a period of ischemia can actually be more damaging than the ischemia. Reintroduction of oxygen causes a greater production of damaging free radicals as well as allowing, via removal of the extracellular acidotic conditions, influx of calcium and thus calcium overloading. Overall this results in reperfusion injury which can result in potentially fatal cardiac arrhythmias, also necrosis can be greatly accelerated. Other existing treatments that address ischemic tissue include hyperbaric oxygen, intravenous thrombolytics, anti-inflammatory agents, and local application of angiogenesis promoters. However, these treatments have generally met with limited success, if any.

Accordingly, there is a substantial need in the art for lower risk, more efficient, and longer lasting therapies that treat tissue damage resulting from ischemia and to ameliorate the symptoms associated therewith.

SUMMARY OF THE INVENTION

The invention generally provides stem and progenitor cell compositions for use in treating ischemic tissue, tissue damaged by ischemia, and/or one or more symptoms of ischemia in a subject. The compositions are more efficient than existing therapies and can be used to treat various types of ischemia. It should be understand that in particular embodiments of the invention, it is contemplated that any two or more embodiments disclosed in the following summary may be used in combination.

In one embodiment, the present invention contemplates, in part, a method of increasing stem or progenitor cell homing to an ischemic tissue or a tissue damaged by ischemia, comprising treating stem or progenitor cells ex vivo with a prostaglandin pathway agonist and optionally, a glucocorticoid, under conditions sufficient to increase CXCR4 gene expression at least two fold in the treated stem or progenitor cells compared to non-treated stem or progenitor cells; and administering a composition comprising the treated stem or progenitor cells to a subject having an ischemic tissue or a tissue damaged by ischemia.

In a particular embodiment, the present invention contemplates, in part, a method of treating a subject having an ischemic tissue or a tissue damaged by ischemia comprising: administering a therapeutically effective amount of a composition comprising stem or progenitor cells treated ex vivo with a prostaglandin pathway agonist and optionally, a glucocorticoid, under conditions sufficient to increase CXCR4 gene expression at least two fold in the treated stem or progenitor cells compared to non-treated stem or progenitor cells.

In certain embodiment, the present invention contemplates, in part, a method of ameliorating at least one symptom associated with an ischemic tissue or a tissue damaged by ischemia in a subject comprising: administering a therapeutically effective amount of a composition comprising stem or progenitor cells treated ex vivo with a prostaglandin pathway agonist and optionally, a glucocorticoid, under conditions sufficient to increase CXCR4 gene expression at least two fold in the treated stem or progenitor cells compared to non-treated stem or progenitor cells.

In one embodiment, the present invention contemplates, in part, a method of increasing stem or progenitor cell homing to an ischemic tissue or a tissue damaged by ischemia, comprising treating stem or progenitor cells ex vivo with a prostaglandin pathway agonist and optionally, a glucocorticoid, under conditions sufficient to increase the percent (%) migration in an SDF-1 transwell migration assay at least two fold in the treated stem or progenitor cells compared to non-treated stem or progenitor cells; and administering a composition comprising the treated stem or progenitor cells to a subject having an ischemic tissue or a tissue damaged by ischemia.

In another particular embodiment, the present invention contemplates, in part, a method of treating a subject having an ischemic tissue or a tissue damaged by ischemia comprising: administering a therapeutically effective amount of a composition comprising stem or progenitor cells treated ex vivo with a prostaglandin pathway agonist and optionally, a glucocorticoid, under conditions sufficient to increase the percent (%) migration in an SDF-1 transwell migration assay at least two fold in the treated stem or progenitor cells compared to non-treated stem or progenitor cells.

In one embodiment, the present invention contemplates, in part, a method of ameliorating at least one symptom associated with an ischemic tissue or a tissue damaged by ischemia in a subject comprising: administering a therapeutically effective amount of a composition comprising stem or progenitor cells treated ex vivo with a prostaglandin pathway agonist and optionally, a glucocorticoid, under conditions sufficient to increase the percent (%) migration in an SDF-1 transwell migration assay at least two fold in the treated stem or progenitor cells compared to non-treated stem or progenitor cells.

In particular embodiments, the stem or progenitor cells have been treated at a temperature of about 22° C. to about 37° C. for a period of time of less than about 24 hours.

In certain embodiments, the stem or progenitor cells have been treated at a temperature of about 22° C. to about 37° C. for a time of about one to about four hours.

In further embodiments, the stem or progenitor cells have been treated at a temperature of about 37° C. for a time of about 4 hours.

In additional embodiments, the stem or progenitor cells are embryonic stem cells.

In other embodiments, wherein the stem or progenitor cells are adult stem cells.

In some embodiments, the stem or progenitor cells are selected from the group consisting of: endothelial stem or progenitor cells, mesodermal stem or progenitor cells, and ectodermal stem or progenitor cells.

In particular embodiments, the stem or progenitor cells are selected from the group consisting of: mesenchymal stem or progenitor cells, hematopoietic stem or progenitor cells, placental stem or progenitor cells, umbilical cord stem or progenitor cells, bone marrow stem cells, and Wharton's jelly stem or progenitor cells.

In certain particular embodiments, the stem or progenitor cells are hematopoietic stem or progenitor cells.

In further particular embodiments, the cells are isolated from peripheral blood, bone marrow, umbilical cord blood, Wharton's jelly, placenta, or fetal blood.

In other particular embodiments, the stem or progenitor cells are CD34+ cells.

In additional particular embodiments, the stem or progenitor cells are, or have been, expanded ex vivo prior to the treatment of the cells.

In some particular embodiments, the stem or progenitor cells are allogeneic or autologous.

In certain embodiments, the stem or progenitor cells are allogeneic and have a complete or partial HLA-match with the patient.

In certain particular embodiments, the stem or progenitor cells are not matched with the patient.

In certain further embodiments, the stem or progenitor cells are xenogeneic.

In certain additional embodiments, the prostaglandin pathway agonist is selected from the group consisting of: a prostaglandin, a prostaglandin $EP_2$ receptor agonist, a prostaglandin $EP_4$ receptor agonist and an agent having 16,16-dimethyl $PGE_2$ ($dmPGE_2$) activity.

In some certain embodiments, the prostaglandin pathway agonist is selected from the group consisting of: prostaglandin $E_2$ ($PGE_2$), and $dmPGE_2$.

In other certain embodiments, the glucocorticoid is selected from the group consisting of: alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, medrysone, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In additional embodiments, the glucocorticoid is selected from the group consisting of: medrysone, hydrocortisone, alclometasone, dexamethasone, methylprednisolone, triamcinolone or Cortisol.

In particular additional embodiments, the prostaglandin pathway agonist is $PGE_2$ or $dmPGE_2$ or an analogue thereof, and the glucocorticoid is medrysone.

In further additional embodiments, expression of one or more genes associated with increased homing of the stem or progenitor cells to the ischemic tissue or tissue damaged by ischemia, is increased at least two fold in the treated stem or progenitor cells compared to non-treated stem or progenitor cells, wherein the one or more genes is selected from the group consisting of: hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), and Fos-related antigen 2 (FOSL2).

In certain additional embodiments, expression of one or more genes associated with increased homing of the stem or progenitor cells to the ischemic tissue or tissue damaged by ischemia, is increased at least two fold in the treated stem or progenitor cells compared to non-treated stem or progenitor cells, wherein the one or more genes is selected from the group consisting of: hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), and CXC chemokine receptor 4 (CXCR4).

In further additional embodiments, the one or more genes is selected from the group consisting of: cAMP-responsive element modulator (CREM) and CXC chemokine receptor 4 (CXCR4).

In other additional embodiments, the one or more genes comprises CXCR4.

In some additional embodiments, the gene expression of at least one of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells.

In further embodiments, the gene expression of at least one of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells.

In certain further embodiments, the gene expression of at least one of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells.

In particular further embodiments, wherein the gene expression of at least one of HAS1, GEM, DUSP4, AREG, NR4A2, REN, CREM, COL1A1, FOSL2, and CXCR4 is increased by at least about fifty fold in the treated stem or progenitor cells compared to non-treated stem or progenitor cells.

In some further embodiments, the gene expression of at least one of HAS1, GEM, DUSP4, AREG, NR4A2, REN, CREM, COL1A1, FOSL2, and CXCR4 is increased by at least about sixty fold in the treated stem or progenitor cells compared to non-treated stem or progenitor cells.

In other further embodiments, the gene expression of at least one of HAS1, GEM, DUSP4, AREG, NR4A2, REN, CREM, COL1A1, FOSL2, and CXCR4 is increased by at least about seventy fold in the treated stem or progenitor cells compared to non-treated stem or progenitor cells.

In yet other further embodiments, the gene expression of at least one of HAS1, GEM, DUSP4, AREG, NR4A2, REN, CREM, COL1A1, FOSL2, and CXCR4 is increased by at least about eighty fold in the treated stem or progenitor cells compared to non-treated stem or progenitor cells.

In particular embodiments, the gene expression of at least two of HAS1, GEM, DUSP4, AREG, NR4A2, REN, CREM, COL1A1, FOSL2, and CXCR4 is increased by at least about two fold in the treated stem or progenitor cells compared to non-treated stem or progenitor cells.

In additional embodiments, the gene expression of at least two of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells.

In other embodiments, the gene expression of at least two of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells.

In some embodiments, the gene expression of at least two of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells.

In further embodiments, the gene expression of at least three of HAS1, GEM, DUSP4, AREG, NR4A2, REN, CREM, COL1A1, FOSL2, and CXCR4 is increased by at least about two fold in the treated stem or progenitor cells compared to non-treated stem or progenitor cells.

In certain embodiments, the gene expression of at least three of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells.

In particular embodiments, the gene expression of at least three of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells.

In some particular embodiments, the gene expression of at least three of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells.

In additional particular embodiments, the gene expression of at least five of HAS1, GEM, DUSP4, AREG, NR4A2, REN, CREM, COL1A1, FOSL2, and CXCR4 is increased by at least about two fold in the treated stem or progenitor cells compared to non-treated stem or progenitor cells.

In certain particular embodiments, the gene expression of at least five of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells.

In further particular embodiments, the gene expression of at least five of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells.

In other particular embodiments, the gene expression of at least five of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells.

In certain embodiments, the % migration of the treated cells in an SDF-1 transwell migration assay is increased at least three fold in the treated stem or progenitor cells compared to non-treated stem or progenitor cells.

In other certain embodiments, the % migration of the treated cells in an SDF-1 transwell migration assay is increased at least three fold in the treated stem or progenitor cells compared to non-treated stem or progenitor cells.

In other particular embodiments, the % migration of the treated cells in an SDF-1 transwell migration assay is increased at least four fold in the treated stem or progenitor cells compared to non-treated stem or progenitor cells.

In further particular embodiments, the % migration of the treated cells in an SDF-1 transwell migration assay is increased at least five fold in the treated stem or progenitor cells compared to non-treated stem or progenitor cells.

In additional further embodiments, the % migration of the treated cells in an SDF-1 transwell migration assay is increased at least ten fold in the treated stem or progenitor cells compared to non-treated stem or progenitor cells.

In certain additional embodiments, the % migration of the treated cells in an SDF-1 transwell migration assay is increased at least twenty fold in the treated stem or progenitor cells compared to non-treated stem or progenitor cells.

In particular certain embodiments, the ischemia is associated with acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, frostbite, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, or wounds to tissues or organs.

In additional particular embodiments, the subject has cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia.

In other particular embodiments, the subject has had surgery, chemotherapy, radiation therapy, or a cell, tissue, or organ transplant.

In certain other embodiments, the ischemic tissue or tissue damaged by ischemia is selected from the group consisting of: skin tissue, skeletal muscle tissue, cardiac muscle tissue, smooth muscle tissue, cartilage tissue, tendon tissue, brain tissue, spinal cord tissue, retinal tissue, corneal tissue, lung tissue, liver tissue, kidney tissue, pancreatic tissue, ovary tissue, testes tissue, intestinal tissue, stomach tissue, and bladder tissue.

In further certain embodiments, the ischemic tissue or tissue damaged by ischemia has decreased blood flow, hypoxia, anoxia, hypoglycemia, decreased metabolism, increased necrosis, or increased apoptosis compared to non-ischemic tissue.

In additional further embodiments, the one or more symptoms associated with the ischemic tissue or tissue damaged by ischemia is selected from the group consisting of: cramping, claudication, numbness, tingling, weakness, pain, reduced wound healing, inflammation, skin discoloration, and gangrene.

In particular additional embodiments, the treated stem or progenitor cells are washed to substantially remove the prostaglandin pathway agonist or glucocorticoid in the composition, prior to administration of the composition to the subject.

In various particular embodiments, the composition comprises hematopoietic stem or progenitor cells, wherein the prostaglandin pathway agonist is 16, 16-dmPGE$_2$ or PGE$_2$, wherein the gene expression of CXCR4 is increased by at least five fold in the treated cells compared to non-treated cells, and wherein the hematopoietic stem or progenitor cells have been contacted with 16, 16-dmPGE$_2$ at a temperature of about 37° C. for a time of about two hours.

In other various embodiments, the composition comprises hematopoietic stem or progenitor cells, wherein the prostaglandin pathway agonist is 16, 16-dmPGE$_2$ or PGE$_2$, wherein the glucocorticoid is selected from the group consisting of medrysone, hydrocortisone, alclometasone, dexamethasone, methylprednisolone, triamcinolone or Cortisol, wherein the gene expression of CXCR4 is increased by at least five fold in the treated cells compared to non-treated cells, and wherein the hematopoietic stem or progenitor cells have been contacted with 16, 16-dmPGE$_2$ at a temperature of about 37° C. for a time of about two hours.

In other particular embodiments, the composition is parenterally administered to the subject.

In certain particular embodiments, the parenteral administration is selected from the group consisting of: intravascular, intramuscular, and subcutaneous.

In additional certain embodiments, the composition is administered intramuscularly at or near a site of the ischemic tissue or tissue damaged by ischemia.

In further additional embodiments, the subject is administered more than one dose of the composition, wherein the doses are separated by a time interval of at least about 24 hours.

In one embodiment, the present invention contemplates, in part, a method of ameliorating at least one symptom associated with ischemia in a subject comprising administering to a subject in need thereof, a therapeutically effective amount of a composition comprising hematopoietic stem and progenitor cells that have been contacted ex vivo with 16, 16-dmPGE$_2$ or PGE$_2$ at a temperature of about 37° C. for a time of about two hours; wherein the gene expression of one or more genes selected from the group consisting of: hyaluronan synthase 1 (HAS 1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), or CXC chemokine receptor 4 (CXCR4) is increased by at least five fold in the contacted hematopoietic stem or progenitor cells compared to the expression of the genes in non-contacted hematopoietic stem or progenitor cells.

In one embodiment, the present invention contemplates, in part, a method of ameliorating at least one symptom associated with ischemia in a subject comprising administering to a subject in need thereof, a therapeutically effective amount of a composition comprising hematopoietic stem and progenitor cells that have been contacted ex vivo with (i) 16, 16-dmPGE$_2$ or PGE$_2$ and (ii) a glucocorticoid selected from the group consisting of medrysone, hydrocortisone, alclometasone, dexamethasone, methylprednisolone, triamcinolone or Cortisol, at a temperature of about 37° C. for a time of about two hours; wherein the gene expression of one or more genes selected from the group consisting of: hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), or CXC chemokine receptor 4 (CXCR4) is increased by at least five fold in the contacted hematopoietic stem or progenitor cells compared to the expression of the genes in non-contacted hematopoietic stem or progenitor cells.

In particular embodiments, the one or more symptoms associated with the ischemic tissue or tissue damaged by ischemia is selected from the group consisting of: cramping, claudication, numbness, tingling, weakness, pain, reduced wound healing, inflammation, skin discoloration, and gangrene.

In one embodiment, the present invention contemplates, in part, a method of treating an ischemic tissue in a subject comprising administering to a subject in need thereof, a therapeutically effective amount of a composition comprising hematopoietic stem and progenitor cells that have been contacted ex vivo with 16, 16-dmPGE$_2$ or PGE$_2$ at a temperature of about 37° C. for a time of about two hours; wherein the gene expression of one or more genes selected from the group consisting of: hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), or CXC chemokine receptor 4 (CXCR4) is increased by at least five fold in the contacted hematopoietic stem or progenitor cells compared to the expression of the genes in non-contacted hematopoietic stem or progenitor cells.

In one embodiment, the present invention contemplates, in part, a method of treating an ischemic tissue in a subject comprising administering to a subject in need thereof, a therapeutically effective amount of a composition comprising hematopoietic stem and progenitor cells that have been contacted ex vivo with (i) 16, 16-dmPGE$_2$ or PGE$_2$, and (ii) a glucocorticoid selected from the group consisting of medrysone, hydrocortisone, alclometasone, dexamethasone, methylprednisolone, triamcinolone or Cortisol, at a temperature of about 37° C. for a time of about two hours; wherein the gene expression of one or more genes selected from the group consisting of: hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), or CXC chemokine receptor 4 (CXCR4) is increased by at least fifty fold in the contacted hematopoietic stem or progenitor cells compared to the expression of the genes in non-contacted hematopoietic stem or progenitor cells.

In various embodiments, the glucocorticoid is medrysone.

DETAILED DESCRIPTION

A. Overview

Figure 1:
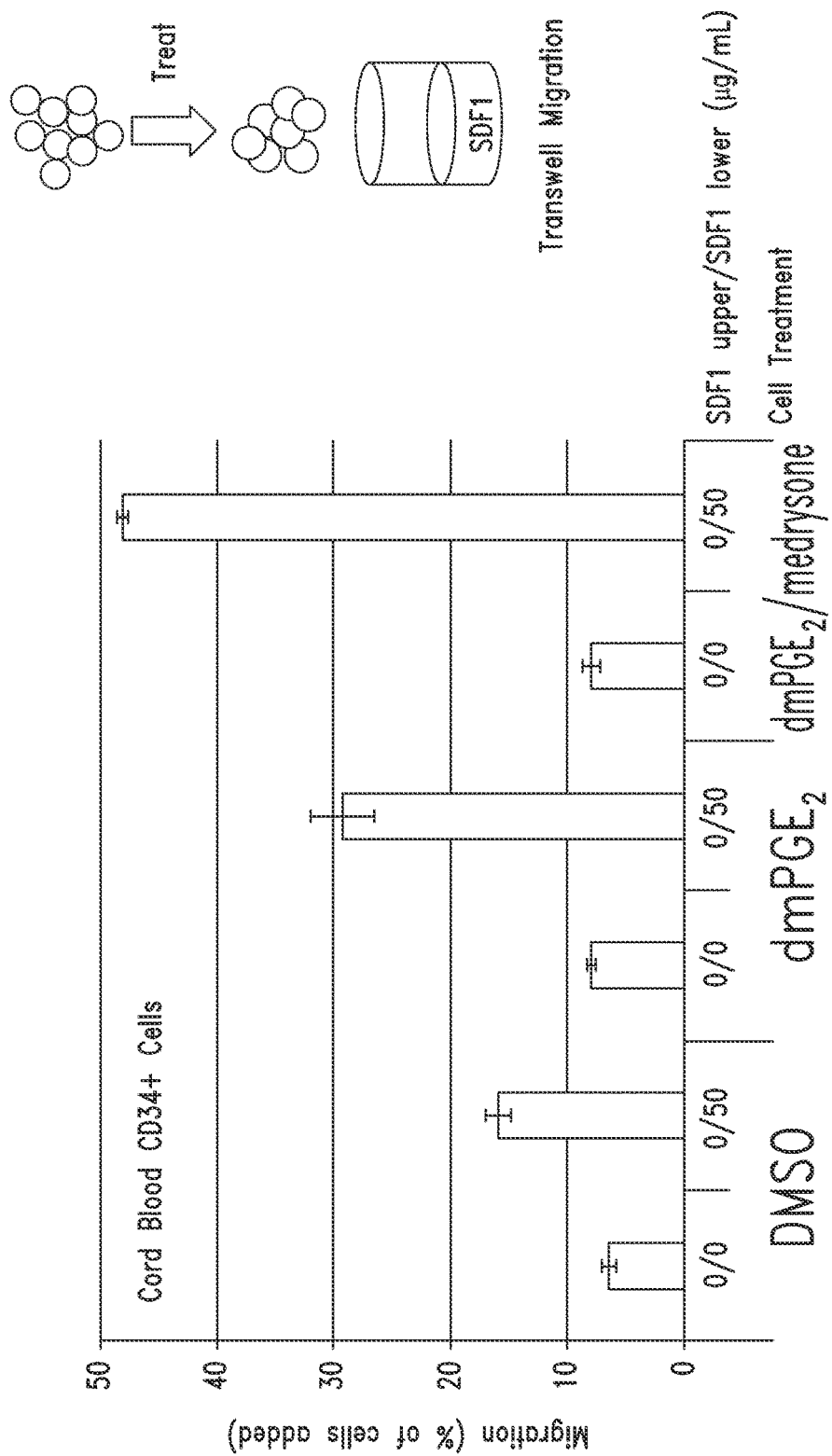
FIG. 1 shows the results from a representative SDF1 transwell migration assay. The results show the effect of treating CD34$^+$ cells with DMSO control, dmPGE$_2$, or dmPGE$_2$ and medrysone on the efficiency of cell migration towards SDF1.

Generally, the invention provides methods to reduce ischemic tissue damage in a subject. Prolonged ischemia results in a lack of oxygen or a "hypoxic" or "anoxic" condition in a cell, tissue, organ, or body part, and if the hypoxic/anoxic conditions persist long enough, ischemia may result in tissue necrosis and/or programmed cell death.

In various embodiments, the invention contemplates, in part, administering an effective amount of a therapeutic composition to a subject to reduce tissue cell damage.

The inventors have developed novel stem and progenitor cells that express high levels of CXCR4 compared to existing therapeutic cells in the art. Without wishing to be bound to any particular theory, the present invention contemplates, in part, that treatment of stem and/or progenitor cells with a prostaglandin pathway agonist, and optionally a glucocorticoid, increases CXCR4 gene expression to high levels and imbues the cells with improved therapeutic properties useful for treating ischemia, such as increased homing to ischemia-damaged tissue, reducing further damage to ischemic tissue and/or repairing damage to ischemic tissue through cell recruitment, improving vascularization in the ischemic tissue, improving tissue regeneration at the ischemic tissue site, decreasing ischemic tissue necrosis or apoptosis, and/or increase cell survival at the ischemic site. In various embodiments, the therapeutic cells are CD34$^+$ cells.

The invention contemplates, in part, administering novel therapeutic compositions comprising stem and progenitor cells that have improved therapeutic properties useful for treating ischemia to a subject in need thereof. Thus, the invention provides a much needed solution to problems that face clinicians that treat patients having ischemia.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

As used herein, the terms "ischemia," "ischemic condition," or "ischemic event" mean any decrease or stoppage in the blood supply to any cell, tissue, organ, or body part caused by any constriction, damage, or obstruction of the vasculature. Ischemia sometimes results from vasoconstriction or thrombosis or embolism. Ischemia can lead to direct ischemic injury, tissue damage due to cell death caused by reduced supply of oxygen (hypoxia, anoxia), glucose, and nutrients. "Hypoxia" or a "hypoxic condition" intends a condition under which a cell, organ or tissue receives an inadequate supply of oxygen. "Anoxia" refers to a virtually complete absence of oxygen in the organ or tissue, which, if prolonged, may result in death of the cell, organ or tissue.

"Symptoms associated with ischemia," "symptoms resulting from ischemia," or "symptoms caused by ischemia" refers to symptoms that include impaired, or loss of, organ function (including without limitation impairments or loss of brain, kidney, or heart function), cramping, claudication, numbness, tingling, weakness, pain, reduced wound healing, inflammation, skin discoloration, and gangrene.

Ischemia can be acute or chronic. "Acute ischemia" means an ischemia that causes symptoms to start abruptly. Acute ischemia can be due to substantial vascular damage and/or evolve from chronic ischemia. Acute ischemia can pose very serious risk to the loss of life or limb in a short period of time. "Chronic ischemia" means that the ischemic condition and symptoms have developed over a relatively long period of time. Chronic ischemia is often associated with genetic diseases, conditions of poor health, e.g., peripheral vascular disease, thromboangiitis obliterans, vasculitis, coronary heart disease and heart failure, atherosclerosis, and diabetes.

Ischemia can also be focal or global. "Focal ischemia" results from the loss of blood flow to a particular vascular region of a tissue or organ. "Global ischemia" results from the loss of blood flow to an entire tissue or organ and is associated with more widespread vascular disruption.

As used herein, the terms "ischemic tissue" or "ischemic organ" and equivalents thereof refer to a tissue or organ that has a decreased blood supply caused by any constriction, damage, or obstruction of the vasculature supplying the tissue or organ.

"Ischemic tissue injury," "ischemic tissue damage," "tissue damage due to ischemia," "tissue damage associated with ischemia," "tissue damage as a result of ischemia," "tissue damaged caused by ischemia," and "ischemic-damaged tissue" refers to morphological, physiological, and/or molecular damage to an organ or tissue or cell as a result of a period of ischemia.

"Hypoxic injury" refers to damage to a cell, organ or tissue due to a period of inadequate oxygen supply. Hypoxic injury often results from an ischemic condition.

A "reperfusion injury" is an injury in which tissue is damaged upon return of blood supply to a tissue or organ after a period of ischemia.

One disease that can cause ischemia is "peripheral vascular disease (PVD)." PVD refers to a condition in which the arteries and/or veins that carry blood to and from the arms, legs, soft tissues and vital organs of the body, including the heart and brain, become narrowed or occluded. This interferes with the normal flow of blood, sometimes causing pain but often causing no readily detectable symptoms. With progression of PVD, significant loss of blood flow to tissue and organs can lead to ischemia, hypoxia, anoxia, tissue death, necrosis and organ death. People with PVD are also at higher risk for heart disease and stroke. Typically most symptomatic PVD is ascribed to "peripheral artery disease" (PAD) denoting the above described pathology predominantly in arteries. The term PVD includes this symptomology and pathology in all classes of blood vessels.

In particular embodiments, compositions of the invention have increased therapeutic properties useful for treating ischemia. As used herein, the term "therapeutic property useful for treating ischemia" refers to increased homing to ischemia-damaged tissue; reducing further damage to ischemic tissue and/or repairing damage to ischemic tissue through cell recruitment, e.g., recruitment of endogenous stem and/or progenitor cells, and/or endothelial progenitor cells; increased vascularization in the ischemic tissue; tissue regeneration at the ischemic tissue site; decreasing ischemic tissue necrosis or apoptosis; and/or increased cell survival at the ischemic site.

"Vascularization" refers to the process of generating new blood vessels in a tissue through neovascularization or angiogenesis. "Neovascularization" refers to the de novo formation of functional microvascular networks in tissues to restore perfusion to a tissue. Neovascularization differs from angiogenesis. "Angiogenesis" is mainly characterized by the protrusion and outgrowth of capillary buds and sprouts from pre-existing blood vessels.

As used herein, the terms "enhance," "improve," "promote," "increase," or "activate" generally refer to the ability of a prostaglandin pathway agonist, optionally in combination with a glucocorticoid, to produce or cause a greater physiological response in a cell, as compared to the response caused by either vehicle or a control molecule/composition, and imbue the cell with improved therapeutic properties e.g., increased homing to ischemia-damaged tissue; reducing further damage to ischemic tissue and/or repairing damage to ischemic tissue through cell recruitment; increased vascularization in the ischemic tissue; tissue regeneration at the ischemic tissue site; decreasing ischemic tissue necrosis or apoptosis; and/or increased cell survival at the ischemic site. An "increased," "improved," or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the terms "decrease," "lower," "lessen," "reduce," or "abate" generally refer to the ability of a prostaglandin pathway agonist, optionally in combination with a glucocorticoid, to produce or cause a lesser physiological response in a cell, as compared to the response caused by either vehicle or a control molecule/composition. In one embodiment, the decrease can be a decrease in gene expression or a decrease in cell signaling that normally is associated with a reduction of cell viability. An "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the terms "maintain," "preserve," "maintenance," "no change," "no substantial change," or "no substantial decrease" generally refers to the ability of a prostaglandin pathway agonist, optionally in combination with a glucocorticoid, to produce or cause a comparable physiological response (i.e., downstream effects) in a cell, as compared to the response caused by either vehicle or a control molecule/composition (reference response). A comparable response is one that is not significantly different or measurably different from the reference response.

In particular embodiments, the therapeutic cells of the invention are prepared by ex vivo or in vitro treatment of the cells.

The term "ex vivo" refers generally to activities or procedures that involve living cells or tissues taken from an organism and cultured in a laboratory apparatus, usually under sterile conditions, and typically for a few hours or up to about 24 hours, but including up to 48 or 72 hours, depending on the circumstances. Tissue culture experiments or procedures lasting longer than a few days using living cells or tissue are typically considered to be "in vitro," though in certain embodiments, this term can be used interchangeably with ex vivo.

The term "treatment," "in vitro treatment," or "ex vivo treatment" generally refers to culturing, contacting, or incubating cells with one or more agents in vitro or ex vivo (i.e., treating the cells). Thus, in particular embodiments, the term "treatment" is used interchangeably with "culturing," "contacting," or "incubating" cells when directed to in vitro or ex vivo cell culture protocols. Cells treated ex vivo are administered to a subject to produce in vivo therapy.

The term "in vivo" refers generally to activities that take place inside an organism, such as cell engraftment, cell homing, self-renewal of cells, and expansion of cells. In one embodiment, the term "in vivo expansion" refers to the ability of a cell population to increase in number in vivo. In particular embodiments, the in vivo expansion include self-renewal and/or proliferation of stem cells.

As used herein, the term "population of cells" refers to a heterogeneous or homogenous population of cells comprising stem and/or progenitor cells. The term "collection of cells" also refers to a population of cells, and in some embodiments is synonymous with "population of cells." However, a collection of cells need not refer to the any particular population of cells. A population of cells can be isolated.

By "isolated" is meant material that is removed from its original environment. A cell is isolated if it is separated from some or all of the components that normally accompany it in its native state.

For example, an "isolated population of cells," an "isolated source of cells," or "isolated hematopoietic stem and progenitor cells and the like, as used herein, refer to in vitro or ex vivo separation of one or more cells from their natural cellular environment, and from association with other components of the tissue or organ, i.e., it is not significantly associated with in vivo substances.

Cells in the therapeutic composition of the invention can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In particular embodiments, the cells of the invention are allogeneic. In certain embodiments, the cells are autologous.

A "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent.

A "progenitor cell" also has the capacity to self-renew and to differentiate into more mature cells, but is committed to a lineage (e.g., hematopoietic progenitors are committed to the blood lineage; myeloid progenitors are committed to the myeloid lineage; lymphoid progenitors are committed to the lymphoid lineage), whereas stem cells are not necessarily so limited.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells). When transplanted into lethally irradiated animals or humans, hematopoietic stem cells can repopulate the erythroid, neutrophil-macrophage, megakaryocyte and lymphoid hematopoietic cell pool.

As used herein, the term "hematopoietic stem and progenitor cell" or "HSPC" refers to a cell identified by the presence of the antigenic marker CD34 and the absence of lineage (lin) markers. HSPCs are therefore characterized as CD34+/Lin(−) cells, and populations of such cells. It is recognized that the population of cells comprising CD34+ and Lin(−) cells also includes hematopoietic progenitor cells, and so for the purposes of this application the term "HSPC" includes hematopoietic progenitor cells.

In particular embodiments, cells of the invention that have surprisingly high levels of CXCR4 expression, have enhanced therapeutic properties, including increased homing to ischemia-damaged tissue; reducing further damage to ischemic tissue and/or repairing damage to ischemic tissue through cell recruitment; increased vascularization in the ischemic tissue; tissue regeneration at the ischemic tissue site; decreasing ischemic tissue necrosis or apoptosis; and/or increased cell survival at the ischemic site.

"Homing" refers to the ability of stem or progenitor cells to localize, i.e., travel, to a particular area or tissue. In particular embodiments, the homing properties of the stem and progenitor cells treated with a prostaglandin pathway agonist, and optionally a glucocorticoid, are increased compared to control, vehicle, or non-treated cells. In one embodiment, cells use a chemoattractant mechanism to home to a particular tissue: cells having increased expression of CXCR4 have improved homing to ischemic tissues secreting stromal cell derived factor 1 (SDF1), the cognate ligand of CXCR4.

In certain embodiments, therapeutic cells of the invention comprise a unique or substantially unique gene signature. As used herein, the term "gene expression profile," "gene expression signature" or "gene signature" refers to the levels of expression of multiple different genes measured for the same sample, i.e., a population of cells. A gene expression signature may be defined so as to identify a group of genes "signature genes" that serves to distinguish the therapeutic cells from existing cells in the art and/or control, vehicle, or non-treated cells.

A "signature gene", as used herein, means any gene in a signature gene set. For example, signature genes include hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), and CXC chemokine receptor 4 (CXCR4). For clarity, signature genes do not include housekeeping genes.

"Gene expression" as used herein refers to the relative levels of expression and/or pattern of expression of a gene in a biological sample, such as the stem and progenitor cells, or population of cells comprising stem or progenitor cells. In particular embodiments, the stem or progenitor cells are hematopoietic stem and progenitor cells.

Any methods available in the art for detecting expression of the genes characterizing the cells comprising the therapeutic composition of the invention are encompassed herein. As used herein, the term "detecting expression" means determining the quantity or presence of an RNA transcript or its expression product of a gene. Methods for detecting expression of genes, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the genes of interest. In some embodiments, PCR-based methods, such as reverse transcription PCR(RT-PCR) (Weis et al., TIG 8:263-64, 1992), and array-based methods such as microarray (Schena et al., Science 270:467-70, 1995) are used.

In various embodiments, the present invention contemplates, in part, administering an effective amount of a therapeutic composition to a subject to reduce tissue cell damage. A "subject" or "subject in need" as used herein, includes any mammal that exhibits at least one symptom of an ischemic tissue or tissue damaged by ischemia, e.g., reduction or blockage of blood flow to the tissue, hypoxic tissue, tissue necrosis or apoptosis, that can be treated or ameliorated by administering a cell-based composition of the present invention. A "subject" also includes a human who is has or who is at risk of having an ischemic tissue or tissue damaged by ischemia, e.g., a subject that has diabetes, peripheral vascular disease, cardiovascular disease, or cerebrovascular disease. Subjects may also include individuals or animals that have undergone a surgical treatment, e.g., an organ transplant or tissue graft. In particular embodiments, a subject receives genetically modified HSPCs as a cell-based gene therapy. In certain embodiments, a subject may have undergone myeloablative irradiation therapy or chemotherapy, or may have experienced an acute radiation or chemcial insult resulting in myeloablation. In certain embodiments, a subject may have undergone irradiation therapy or chemotherapy, such as during various cancer treatments. Suitable subjects (e.g., patients) include laboratory animals (e.g., mouse, rat, rabbit, or guinea pig), farm animals, and domestic animals or pets (e.g., a cat or dog). Non-human primates and, preferably, human patients, are included.

As used herein, the terms "treat," "treatment," "treating," and the like, refer to obtaining a desired pharmacologic and/or physiologic effect, including without limitation achieving amelioration, improvement, or elimination of symptoms of ischemia. The effect may be prophylactic in terms of completely or partially preventing ischemic tissue damage and/or may be therapeutic in terms of ameliorating, improving, or eliminating one or more symptoms of an ischemic tissue or tissue damaged by ischemia. "Treatment," as used herein, covers any treatment of an ischemic condition in a mammal, particularly in a human, and includes: (a) preventing the ischemia from occurring in a subject which may be predisposed to the ischemia but has not yet been diagnosed as having it; (b) inhibiting the ischemia or preventing further ischemic tissue damage, i.e., arresting its development; (c) relieving the ischemia, e.g., causing revascularization of the tissue, e.g., to completely or partially eliminate symptoms of the ischemia; and (d) restoring the individual to a pre-disease state, e.g., complete revascularization of the previously ischemic tissue. "Treatment" may not indicate, or require, complete eradication or cure of the ischemia, or associated symptoms thereof. In particular methods of the invention, treatment or treating provides improved blood flow to an ischemic tissue, improved oxygenation of an ischemic tissue, improved vascularization of an ischemic tissue, and improved survival of ischemic tissue.

The articles "a," "an," and "the" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

"Substantially" refers to a quantity, level, value, number, frequency, percentage, dimension, size, amount, weight or length that is nearly equivalent to a reference quantity, level, value, number, frequency, percentage, dimension, size, amount, weight or length. In particular embodiments, nearly equivalent can be the reference value plus or minus 15%, 10%, 5%, or 1%.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

C. Compositions

In numerous embodiments, the methods of the invention comprise administration of compositions to a subject in order to treat ischemic tissue damage in the subject. In various embodiments, the methods of the present invention comprise administration of compositions to a subject in order to treat or ameliorate at least one symptom associated with an ischemic tissue.

To this end, the inventors have developed novel stem and progenitor cells that express high levels of CXCR4, thereby producing therapeutic cells with improved properties useful for treating ischemia, such as increased homing to ischemia-damaged tissue, reducing further damage to ischemic tissue and/or repairing damage to ischemic tissue through cell recruitment, improving vascularization in the ischemic tissue, improving tissue regeneration at the ischemic tissue site, decreasing ischemic tissue necrosis or apoptosis, and/or increasing cell survival at the ischemic site.

Thus, the invention contemplates, in part, compositions, e.g., therapeutic compositions, comprising stem or progenitor cells, e.g., hematopoietic stem or progenitor cells, that have been treated, e.g., cultured, contacted, or incubated, ex vivo with a prostaglandin pathway agonist or a prostaglandin pathway agonist and a glucocorticoid. The cells are treated with the agents in an amount effective and for a time sufficient to cause an increase in CXCR4 expression in the cells compared to non-contacted cells or cells contacted with a control or vehicle (e.g., DMSO). In preferred embodiments, the increase in CXCR4 expression in the treated cells, identifies the cells as those having improved therapeutic properties useful for treating ischemic tissue or treating and/or ameliorating at least one symptom associated with an ischemic tissue.

In particular embodiments, the compositions further comprise one or more pharmaceutically acceptable carriers, diluents, or components as described elsewhere, infra.

1. Stem or Progenitor Cells

In particular embodiments, methods of the present invention comprise administering a therapeutic composition comprising stem or progenitor cells to a subject, wherein the stem or progenitor cells have been treated with one or more prostaglandin pathway agonists and/or one or more glucocorticoids. The treated cells have the properties of increased homing to sites of ischemic tissue damage, increased recruitment of endogenous stem cells and endothelial progenitor cells, increased stimulation of vascularization at the ischemic tissue site, and reduction of ischemic tissue necrosis and/or programmed cell death. The treated stem or progenitor cells can be adult cells or embryonic cells.

In various embodiments, the stem and/or progenitor cells administered to the subject are HLA matched to the subject. There are six major HLA antigens (HLA-A, HLA-B, HLA-C, HLA-DR, HLA-DP, and HLA-DQ). Each HLA antigen has multiple isoforms in the human population, and each individual can have two different isoforms for each HLA due to the diploid nature of our genome. Therefore, a complete match would match twelve out of twelve isoforms.

HLA-type can be determined using so-called low resolution methods, for example by sero-typing, or using antibody based methods. Sero-typing is based on antibody recognition of HLA-types. Sero-typing can distinguish between 28 different HLA-A genes, 59 HLA-B genes and 21 HLA-C genes. A perfect match by sero-typing methods would be a so-called six out of six match referring to the two alleles for each HLA (A, B, and C) present in each individual. In certain cases, a five out of six match or less may be considered a good match as determined by one skilled in the art. In some embodiments, the population of HLA haplotyped cells has 3/6, 4/6, 5/6, or 6/6 HLA matches with a specific human subject. HLA matching may be based on alleles or antigens, and combinations thereof.

The therapeutic composition of the invention is capable of obtaining product licensure from the FDA (i.e., FDA approval) and other health authorities in other countries and regulatory territories, as well as product labeling with characterizing information regarding product indication, product efficacy, safety and purity.

a. Types of Stem and Progenitor Cells

Various types of stem and progenitor cells are suitable for use in the particular methods of the present invention, including, but not limited to, embryonic stem cells, mesodermal stem or progenitor cells, endodermal stem or progenitor cells, and ectodermal stem or progenitor cells. Other suitable stem or progenitor cells suitable for use in the methods of the present invention include, but are not limited to, mesodermal cells such as mesenchymal stem or progenitor cells, hematopoietic stem or progenitor cells, placental stem or progenitor cells, umbilical cord stem or progenitor cells, bone marrow stem cells, and Wharton's jelly stem or progenitor cells.

In preferred embodiments, hematopoietic stem or progenitor cells are used in the methods of the present invention. In other preferred embodiments, $CD34^+$ cells are used in the methods of the present invention.

In various embodiments, a heterogeneous population of cells comprising hematopoietic stem or progenitor cells or $CD34^+$ cells is treated with a prostaglandin pathway agonist and/or one or more glucocorticoids, as described elsewhere herein, and subsequently administered to a subject. Exemplary heterogeneous populations of cells include, but are not limited to, whole bone marrow, umbilical cord blood, mobilized peripheral blood, hematopoietic stem cells, placenta, placental blood, and Wharton's jelly.

In one embodiment, the therapeutic composition comprises a cell population that is about 75%, about 80%, about 85%, about 90%, about 95%, or about 100% hematopoietic stem and progenitor cells or $CD34^+$ cells. In some embodiments, the population of cells in the therapeutic composition is less than about 0.1%, 0.5%, 1%, 2%, 5%, 10%, 15%, 20%, 25%, or 30% hematopoietic stem and progenitor cells or $CD34^+$ cells.

HSCs may be identified according to certain phenotypic or genotypic markers. Most human HSCs may be characterized as $CD34^+$, $CD59^+$, $Thy1/CD90^+$, $CD381^{o/-}$, C-kit/$CD117^+$, and Lin(−). However, not all stem cells are covered by these combinations, as certain HSCs are $CD34^-/CD38^-$. Also some studies suggest that earliest stem cells may lack c-kit on the cell surface. For human HSCs, CD133 may represent an early marker, as both $CD34^+$ and $CD34^-$ HSCs have been shown to be $CD133^+$. It is known in the art that $CD34^+$ and Lin(−) cells also include hematopoietic progenitor cells and HSPCs.

Kits are commercially available for purifying stem and progenitor cells from various cell sources and in particular embodiments, these kits are suitable for use with the methods of the present invention. Exemplary commercially available kits for purifying stem and progenitor cells include, but are not limited to Lineage (Lin) Depletion Kit (Miltenyi Biotec); $CD34^+$ enrichment kit (Miltenyi Biotec); RosettaSep (Stem Cell Technologies).

In particular embodiments, the population of cells comprises hematopoietic stem or progenitor cells or $CD34^+$ cells and is substantially free of mesenchymal stem cells and/or endothelial progenitor cells. In certain embodiments, the population of cells comprises hematopoietic stem or progenitor cells or $CD34^+$ cells less than about 30%, 25%, 20%, 15%, 10% or 5% mesenchymal stem cells and less than about 30%, 25%, 20%, 15%, 10% or 5% endothelial progenitor cells.

Populations of cells may alternatively be depleted of mesenchymal stem cells and/or endothelial progenitor cells using methods known in the art, for example, using immunomagnetic selection techniques, fluorescence activated cell sorting, or a combination therein, $CD34^+$ cells may be purified from any number of cell sources disclosed herein and suitable for use in the present invention.

b. Source of Stem and Progenitor Cells

Suitable sources of stem and progenitor cells for use in the methods of the present invention include, but are not limited to, cells isolated or obtained from an organ or tissue of the body containing cells of mesodermal, endodermal, or ectodermal origin. The stem and progenitor cells used in the invention can be obtained by conventional means known to those of skill in the art. In some embodiments, commercially available stem and progenitor cell lines can be used in the methods of the invention.

In one embodiment, stem and progenitor cells for use in the therapeutic compositions and methods of the invention can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the terms "reprogramming" refers to a method of increasing the potency of a cell to a less differentiated state. As used herein, the term "programming" refers to a method of decreasing the potency of a cell or differentiating the cell to a more differentiated state.

Hematopoietic stem and progenitor cells can be isolated from a variety of sources including, but not limited to, peripheral blood, bone marrow, umbilical cord blood, Wharton's jelly, placenta, fetal blood, fetal liver, or fetal spleen. In particular embodiments, the hematopoietic stem or progenitor cells are harvested or mobilized from a hematopoietic source. "Harvesting" refers to dislodging or separating hematopoietic stem and progenitor cells from the matrix by using, e.g., enzymatic treatment, centrifugal, electrical, or size-based methods, or preferably, by flushing the cells using media (e.g., media in which the cells are incubated). "Hematopoietic stem cell mobilization" refers to the release of stem cells from the bone marrow into the peripheral blood circulation for the purpose of leukapheresis, prior to stem cell transplantation. Hematopoietic growth factors, e.g., granulocyte colony stimulating factor (G-CSF), Mozobil™ (Genzyme Corporation), or chemotherapeutic agents often are used to stimulate the mobilization.

c. Culture of Stem or Progenitor Cells

Stem and/or progenitor cells, e.g., hematopoietic stem and/or progenitor cells may be grown, treated or expanded in any suitable, commercially available or custom defined medium, with or without serum, as desired (see, e.g., Hartshorn et al., Cell Technology for Cell Products, pages 221-224, R. Smith, Editor; Springer Netherlands, 2007, herein incorporated by reference in its entirety).

For example, in certain embodiments, serum free medium may utilize albumin and/or transferrin, which have been shown to be useful for the growth and expansion of $CD34^+$ cells in serum free medium. Also, cytokines may be included, such as Flt-3 ligand, stem cell factor (SCF), and thrombopoietin (TPO), among others. Hematopoietic stem and progenitor cells may also be grown in vessels such as bioreactors (see, e.g., Liu et al., Journal of Biotechnology 124:592-601, 2006, herein incorporated by reference in its entirety). A suitable medium for ex vivo expansion of HSPCs may also comprise HSPC supporting cells, such as stromal cells (e.g., lymphoreticular stromal cells), which can be derived, for instance, from the disaggregation of lymphoid tissue, and which have been show to support the in vitro, ex vivo, and in vivo maintenance, growth, and differentiation of HSPCs, as well as their progeny.

d. Treatment of Stem or Progenitor Cells

Stem and progenitor cells of the invention are treated, e.g., contacted, cultured, or incubated with a prostaglandin pathway agonist or a prostaglandin pathway agonist and a glucocorticoid. Without wishing to be bound to any particular theory, cells treated in this manner are imbued with improved therapeutic properties compared to control, vehicle, or non-treated cells.

The cells may be treated with agents disclosed herein after isolation from a subject. In another embodiment, cells are isolated from a subject and expanded prior to treatment with the agents disclosed herein. In one embodiment, the cells are isolated from a subject and cryopreserved prior to treatment with the agents disclosed herein.

In preferred embodiments, stem and progenitor cells are treated with one or more agents, e.g., a prostaglandin pathway agonist or a prostaglandin pathway agonist and a glucocorticoid in an amount effective and for a time sufficient (i.e., under conditions sufficient) to enhance therapeutic properties of the cells, e.g., increased homing to sites of ischemic tissue damage, increased recruitment of endogenous stem cells and endothelial progenitor cells, increased stimulation of vascularization at the ischemic tissue site, and reducing ischemic tissue necrosis and/or programmed cell death. As mentioned elsewhere herein, treated cells with enhanced therapeutic properties can be identified, for example, by gene expression, e.g., increased expression of CXCR4 and/or a particular group of signature genes; increased expression of CXCR4 protein and/or a particular group of signature genes; intracellular cAMP signaling, e.g., CREB phosphorylation, or as determined by a biochemical assay; or by functional assay, e.g., transwell migration assay.

As used herein, the terms "conditions sufficient," or "under conditions sufficient," refer to the conditions for treating the stem and/or progenitor cells, e.g., hematopoietic stem and progenitor cells, with one or more agents, e.g., prostaglandin pathway agonist, optionally in combination with a glucocorticoid to increase CXCR4 gene expression and/or expression of a group of signature genes in the cells to surprising an unexpected levels compared to control, vehicle, or non-treated cells.

In one embodiment, the conditions are sufficient to increase therapeutic properties of the cells in vivo, such as, for example, to increase stem and progenitor cell homing to sites of ischemic tissue damage, to increase recruitment of endogenous stem cells and endothelial progenitor cells to sites of ischemic tissue damage, to increase vascularization at the ischemic tissue site, and to reduce ischemic tissue necrosis and/or programmed cell death, and/or increase cell survival at the ischemic tissue site.

Conditions include, but are not limited to source of the cells, agent(s) concentration, the time the cells are exposed to the agent(s), and the temperature. In particular embodiments, the cells are contacted with one or more agent(s): a prostaglandin pathway agonist, e.g., $PGE_2$, $dmPGE_2$, 15(S)-15-methyl $PGE_2$, 20-ethyl $PGE_2$, 8-iso-16-cyclohexyl-tetra-nor $PGE_2$, and $PGE_2$ analogues; or a prostaglandin pathway agonist and a glucocorticoid. In one embodiment, the one or more agents are $PGE_2$ or 16,16-dimethyl $PGE_2$. In another embodiment, the one or more agents include (i) $PGE_2$ or 16,16-dimethyl $PGE_2$ and (ii) medrysone, hydrocortisone, dexamethasone, methylprednisolone, triamcinolone, or alclometasone.

In various embodiments, sufficient temperature conditions include, incubation at a physiologically relevant temperature, such as a temperature range of about 39° C. (about room temperature to about body temperature), including but not limited to temperatures of about 22° C., 23° C., 24° C., 25° C., 26° C., 27° C., 28° C., 29° C., 30° C., 31° C., 32° C., 33° C., 34° C., 35° C., 36° C., 37° C., 38° C., and 39° C. In a particular embodiment, the sufficient temperature condition is between about 35° C. and 39° C. In one embodiment, the sufficient temperature condition is about 37° C.

In various embodiments, the sufficient concentration of agent(s) is a final concentration of about 10 nM to about 100 µM, about 100 nM, about 500 nM, about 1 µM, about 10 µM, about 20 µM, about 30 µM, about 40 µM, about 50 µM, about 60 µM, about 70 µM, about 80 µM, about 90 µM, about 100 µM, about 110 µM, or about 120 µM, or any other intervening concentration of 16,16-dimethyl $PGE_2$ (e.g., 0.1 µM, 1 µM, 5 µM, 10 µM, 20 µM, 50 µM, 100 µM). In a particular embodiment, the sufficient concentration of agent(s) is a final concentration of about 10 µM to about 25 µM. In one embodiment, the sufficient concentration of agent(s) is a final concentration of about 10 µM.

In various embodiments, the sufficient time period for treating the cells is a duration of about 60 minutes to about twelve hours, 60 minutes to about 6 hours, about 2 hours to about 4 hours, including but not limited to treatment for a duration of about 60 minutes, about 70 minutes, about 80 minutes, about 90 minutes, about 100 minutes, about 110 minutes, about 2 hours, about 2.5 hours, about 3 hours, about 3.5 hours or about 4 hours or any other intervening duration. In a particular embodiment, the sufficient duration of time for treating the cells is about 2 hours to about 4 hours. In one embodiment, the sufficient duration for treating the cells is about four hours.

In particular embodiments, conditions sufficient to increase one or more therapeutic properties of the treated cells in vivo, include, incubation at a temperature range of about 22° C. to about 39° C.; a final concentration of about 10 µM to about 25 µM of a prostaglandin pathway agonist, and optionally a glucocorticoid; and incubation for about 1 hour to about 4 hours, for about 2 hours to about 3 hours, for about 2 hours to about 4 hours, or for about 3 hours to about 4 hours.

In another embodiment, conditions sufficient to increase one or more therapeutic properties of the treated cells in vivo, include, incubation at a temperature of about 37° C. (about body temperature); a final concentration of about 10 µM $PGE_2$ or 16,16-dimethyl $PGE_2$, optionally in combination with a final concentration of about 10 µM medrysone; and incubation for about four hours.

In particular embodiments, a stem and/or progenitor cells are treated (e.g., contacted with one or more agents) 1, 2, 3, 4, 5, 6, 7, 8, 9 or 10 or more times. Cells can be intermittently, episodically, or sequentially contacted with one or more agents within the same vessel (e.g., contacting the population of cells with one drug for a period of time, exchanging the culture medium and/or washing the population of cells, then repeating the cycle with the same or a different combination of pharmaceutical agents for the same predetermined period of time or a different predetermined period of time).

2. CXCR4 Expression/Gene Expression Profile of Stem or Progenitor Cells

The therapeutic compositions comprise a population of treated stem or progenitor cells having increased therapeutic properties related to the treatment of ischemic tissue. Without wishing to be bound to any particular theory, treatment of the cells with a prostaglandin pathway agonist and/or a glucocorticoid imbues the cells with the increased therapeutic properties useful for treating ischemic tissue or more or more symptoms associated with an ischemic tissue. Cells that have the increased therapeutics properties are characterized by increased CXCR4 gene expression and increased cell surface expression of CXCR4 polypeptide. In a particular embodiment, the therapeutic composition comprises hematopoietic stem or progenitor cells characterized by increased levels of gene and cell-surface CXCR4 expression.

Stem or progenitor cells, e.g., hematopoietic stem or progenitor cells, treated with a prostaglandin pathway agonist can be characterized by at least a 2, 3, 4, 5, 10, 15, or 20 fold increase in CXCR4 gene expression compared to the expression of CXCR4 in untreated cells.

Stem or progenitor cells, e.g., hematopoietic stem or progenitor cells, treated with a prostaglandin pathway agonist and a glucocorticoid can be characterized by at least a 40, 45, 50, 55, 60, 65, 70, 75, or 80 fold increase in CXCR4 gene expression compared to the expression of CXCR4 in untreated cells.

Cells that have increased therapeutic properties related to the treatment of ischemic tissue can further characterized by a unique gene expression signature wherein expression of 1, 2, 3, 4, 5, 6, 7, 8, 9, or all 10 of the signature genes selected from the group consisting of: CXCR4, hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), and Fos-related antigen 2 (FOSL2) is increased, compared to untreated cells.

In particular embodiments, hematopoietic stem or progenitor cells treated with a prostaglandin pathway agonist have a gene expression signature, wherein 1, 2, 3, 4, 5, 6, 7, 8, 9, 10 or more of the signature genes is increased by at least 2, 3, 4, 5, 6, 10, 15, or 20 fold compared to untreated cells. In some embodiments, the average fold change of all signature genes is at least about 2, 3, 4, 5, or 6 fold. In some embodiments, the average fold change of all signature genes is at least about 6.

In other particular embodiments, hematopoietic stem or progenitor cells treated with a prostaglandin pathway agonist and a glucocorticoid have a gene expression signature, wherein 1, 2, 3, 4, 5, 6, 7, 8, 9, 10 or more of the signature genes is increased by at least 40, 45, 50, 55, 60, 65, 70, 75, or 80 fold compared to untreated cells. In some embodiments, the average fold change of all signature genes is at least about 15, 20, 25, 30, or 35 fold. In some embodiments, the average fold change of all signature genes is at least about 25.

The gene expression or gene expression signature of the treated stem or progenitor cells may be determined after cells are treated with an agent, or cells may be incubated for some period of time after treatment before determining the gene expression signature of the cells. For example, cells may be treated ex vivo with an agent, washed to remove the agent, and the gene expression analyzed without further incubation of the cells. Alternatively, in some embodiments, cells are treated with an agent, washed to remove the agent from the cell population, and then the cells are incubated ex vivo for some period of time prior to analyzing the gene expression signature of the cells.

D. Agents

In various embodiments, the invention provides a therapeutic composition comprising stem or progenitor cells contacted with one or more agents capable of increasing CXCR4 gene expression in the cells, including agents that stimulate the prostaglandin pathway, e.g., the $PGE_2R_2/R_4$ cell signaling pathway, optionally in combination with one or more glucocorticoids. In preferred embodiments, the cells are hematopoietic stem and progenitor cells.

As used herein, "agent" refers to a compound capable of stimulating the prostaglandin pathway, e.g., prostaglandin pathway agonist. Agent also refers to a glucocorticoid, described infra. In particular embodiments, an agent increases CXCR4 expression in the treated cells. In certain embodiments, stem or progenitor cells are contacted with 1, 2, 3, 4, 5 or more agents in any combination, simultaneously or sequentially under conditions sufficient to increase CXCR4 expression and/or increase one or more therapeutic properties of the cells in vivo, e.g., increased homing to sites of ischemic tissue damage, increased recruitment of endogenous stem cells and endothelial progenitor cells, increased stimulation of vascularization at the ischemic tissue site, reducing ischemic tissue necrosis and/or programmed cell death, and increasing cell survival at the site of ischemic tissue damage.

Agents are prepared using cGMP practices, can be formulated in an organic solvent, such as methyl acetate, for use in contacting the cells of the invention, and may be supplied in an endotoxin free vessel.

1. Prostaglandin Pathway Agonists

Prostaglandin $E_2$ ($PGE_2$) exerts its function by acting on a number of different prostaglandin receptors on various cell types, activating various signaling pathways including, without limitation, the PI3-kinase (PI3-K or PI3K) pathway. These prostaglandin receptors represent a sub-family of the cell surface seven-transmembrane receptors referred to as G-protein-coupled receptors (GPCRs). There are four sub-types of prostaglandin $E_2$ receptors, $PGE_2R_1$, $PGE_2R_2$, $PGE_2R_3$ and $PGE_2R_4$. When activated by a suitable ligand, or agonist, such as a prostaglandin or analogue thereof, e.g., a $PGE_2R_2$ or $PGE_2R_4$ agonist, these prostaglandin receptors initiate a variety of downstream biological functions. For example, stimulation/activation of $PGE_2R_2$ and/or $PGE_2R_4$ cell signaling in stem and progenitor cells is coupled, in part, to G-protein alpha-s (Gα-s or Gα-s) activation and stimulation of adenylate cyclase and to the Wnt pathway (North et al., *Nature* 447(7147): 1007-11 (2007)).

In various embodiments, the invention contemplates a therapeutic composition comprising stem or progenitor cells contacted with one or more prostaglandin pathway agonists.

As used herein, the term "prostaglandin pathway agonist" refers to an agent that stimulates prostaglandin cell signaling pathways, including an agent that stimulates the $PGE_2R_2$ and/or $PGE_2R_4$ cell signaling pathways, and increases $CXCR_4$ gene expression in the cells and improves one or more therapeutic properties of the cell in vivo, e.g., increased homing to sites of ischemic tissue damage, increased recruitment of endogenous stem cells and endothelial progenitor cells, increased vascularization at the ischemic tissue site, reducing ischemic tissue necrosis and/or programmed cell death, and increasing cell survival at the ischemic tissue site. Illustrative examples of prostaglandin pathway agonists that are suitable for use in treating cells of the invention, include, but are not limited to, $PGE_2$, $dmPGE_2$, 15(S)-15-methyl $PGE_2$, 20-ethyl $PGE_2$, 8-iso-16-cyclohexyl-tetranor $PGE_2$, and $PGE_2$ analogues. In certain embodiments, $PGE_2R_2$ and $PGE_2R_4$ agonists and analogues thereof are of particular interest, and in some embodiments, the agent preferentially binds and activates a $PGE_2$ $EP_2$ or $PGE_2$ $EP_4$ receptor.

Illustrative examples of prostaglandin pathway agonists that are suitable for use in treating cells of the invention, also include, but are not limited to, $PGE_2$, $dmPGE_2$, and $PGE_2$ analogues. In certain embodiments, $PGE_2R_4$ agonists and analogues thereof are of particular interest, and in some embodiments, the agent preferentially binds and activates a $PGE_2$ $EP_4$ receptor.

As used herein, the terms "prostaglandin $E_2$" or "$PGE_2$" include, without limitation, any naturally-occurring or chemically synthesized $PGE_2$ molecule, as well as "analogues" thereof. As used herein, the term "analogue" relates to a chemical molecule that is similar to another chemical substance, e.g., $PGE_2$, in structure and function, often differing structurally by a single element or group, but may differ by modification of more than one group (e.g., 2, 3, or 4 groups) if it retains the same function as the parental chemical.

Illustrative examples of $PGE_2$ "analogues" include, without limitation, 16,16-dimethyl $PGE_2$ ($dmPGE_2$), 16,16-dimethyl $PGE_2$ p-(p-acetamidobenzamido)phenyl ester, 11-deoxy-16,16-dimethyl $PGE_2$, 9-deoxy-9-methylene-16,16-dimethyl $PGE_2$, 9-deoxy-9-methylene $PGE_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso $PGE_2$ isopropyl ester, 20-hydroxy $PGE_2$, 11-deoxy $PGE_1$, nocloprost, sulprostone, butaprost, 15-keto $PGE_2$, and 19 (R) hydroxy $PGE_2$.

Agents selective for the $PGE_2$ $EP_4$ receptor preferentially bind to $PGE_2$ $EP_4$ receptor have a higher affinity for the $EP_4$ receptor than for any of the other three EP receptors namely $EP_1$, $EP_2$ and $EP_3$. Illustrative agents that selectively bind the $PGE_2$ $EP_4$ receptor include, but are not limited to, agents selected from the group consisting of: 5-[(1E,3R)-4,4-difluoro-3-hydroxy-4-phenyl-1-buten-1-yl]-1-[6-(2H-tetrazol-5R-yl)hexyl]-2-pyrrolidinone; 2-[3-[(1R,2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3S)-3-hydroxy-4-[3-(methoxymethyl)phenyl]but-1-enyl]-5-oxocyclopentyl]ethylsulfanyl]butanoate; 16-(3-M ethoxymethyl)phenylro-tetranor-5-thiaPGE; 5-{3-[(2S)-2-{(3R)-3-hydroxy-4-[3-(trifluoromethyl)phenyl]butyl}-5-oxopyrrolidin-1-yl] propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid).

In particular embodiments, the prostaglandin pathway agonist is $PGE_2$, $dmPGE_2$, 15(S)-15-methyl $PGE_2$, 20-ethyl $PGE_2$, or 8-iso-16-cyclohexyl-tetranor $PGE_2$.

In a preferred embodiment, the stem or progenitor cells, e.g., hematopoietic stem or progenitor cells, are treated (contacted) with a prostaglandin pathway agonist selected from the group consisting of: $PGE_2$ or $dmPGE_2$, optionally in combination with a glucocorticoid.

2. Glucocorticoids

Glucocorticoids are essential to life and after removal of both adrenal glands mammals will not survive for long without glucocorticoid replacement. Receptors for glucocorticoids (GRs) are usually intracellular and exist in the cytoplasm, not the nucleus, and are associated with heat shock proteins (HSPs). The HSPs are displaced when glucocorticoids diffuse across the cell membrane, and bind to the GR. Subsequent phosphorylation of the glucocorticoid-GR complex facilitates translocation of the complex into the nucleus where it forms a homo- or heterodimer with another hormone-receptor complex. The zinc fingers in the DNA-binding domain of the dimerized receptors interact with glucocorticoid response element (GRE) to stimulate or suppress gene transcription that is usually initiated down-stream of the GRE.

The present inventors have unexpectedly discovered that treating stem and/or progenitor cells with a prostaglandin pathway agonist and a glucocorticoid results in surprisingly high increase in the therapeutic properties of the treated cells compared to control, vehicle, or non-treated cells. In particular, treatment of stem and/or progenitor cells with a prostaglandin agonist and a glucocorticoid increases CXCR4 expression, increases the expression of one or more signature genes, and increases one or more therapeutic properties of the cells in vivo, e.g., increased homing to sites of ischemic tissue damage, increased recruitment of endogenous stem cells and endothelial progenitor cells, increased stimulation of vascularization at the ischemic tissue site, reducing ischemic tissue necrosis and/or programmed cell death, or increasing cell survival at the ischemic tissue site.

Illustrative examples of glucocorticoids and glucocorticoid receptor agonists suitable for use in the methods of the present invention include, but are not limited to, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, medrysone, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol.

In a particular embodiment, the stem or progenitor cells, e.g., hematopoietic stem or progenitor cells are treated (contacted) with a prostaglandin pathway agonist, in combination with a glucocorticoid selected from the group consisting of: cortisol, cortisone acetate, prednisone, prednisolone, methylprednisolone, dexamethasone, betamethasone, triamcinolone, beclometasone, fludrocortisone acetate, deoxycorticosterone acetate, and aldosterone.

In one embodiment, the stem or progenitor cells, e.g., hematopoietic stem or progenitor cells are treated (contacted) with a prostaglandin pathway agonist selected from the group consisting of: $PGE_2$ or $dmPGE_2$, in combination with a glucocorticoid selected from the group consisting of: medrysone, hydrocortisone, alclometasone, dexamethasone, methylprednisolone, or triamcinolone.

In a preferred embodiment, the stem or progenitor cells, e.g., hematopoietic stem or progenitor cells are treated (contacted) with $PGE_2$ or $dmPGE_2$, optionally in combination with medrysone.

E. Administration

The compositions of the invention are sterile, and are suitable and ready for administration (i.e., can be administered without any further processing) to human subjects. In some embodiments, the composition is ready for infusion into a subject. As used herein, the terms "administration-ready," "ready for administration" or "ready for infusion" refer to a cell based composition of the invention that does not require any further treatment or manipulations prior to administration to a subject.

Suitable methods for administering populations of cells used in the methods described herein include parenteral administration, including, but not limited to methods of intravascular administration, such as intravenous and intraarterial administration. Additional illustrative methods for administering cells of the invention include intramuscular, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

In particular embodiment, the composition may be administered topically to a site of ischemic tissue damage, such as, for example, the surface of a wound, e.g., a non-healing wound, an ulcer, a burn, or frostbite.

Most preferably, the site of administration is close to or nearest the intended site of activity, i.e., near the site of tissue ischemia. In cases when a subject suffers from global ischemia, a systemic administration, such as intravenous administration, is preferred. Without intending to be bound by mechanism, when the therapeutic compositions are administered, the stem and progenitor cells migrate or home to the ischemic tissue in response to chemotactic factors produced due to the injury to effect treatment of ischemic tissue or treatment and amelioration of at least one symptom associated with the ischemic tissue.

The stem cells can be injected directly into the area of ischemia, or the stem cells may be infused into an artery supplying the area of tissue ischemia. Where the subject has a totally occluded vessel that would normally supply the area of the ischemic tissue, the selected artery for infusion is preferably a vessel that provides collateral flow to the ischemic tissue in the distribution of the totally occluded vessel.

In particular illustrative embodiments of the methods described herein for treating or ameliorating ischemia to at least one symptom of ischemia, comprise intravenously administering or directly injecting HSPCs to a subject.

Cells may be inserted into a delivery device which facilitates introduction by injection or implantation into the subjects. Such delivery devices may include tubes, e.g., catheters, for injecting cells and fluids into the body of a recipient subject. In one embodiment, the tubes additionally have a needle, e.g., a syringe, through which the cells of the invention can be introduced into the subject at a desired location. In a particular embodiment, cells are formulated for administration into a blood vessel via a catheter (where the term "catheter" is intended to include any of the various tube-like systems for delivery of substances to a blood vessel).

F. Dose and Formulation

In various embodiments, the invention contemplates administration of the therapeutic composition to a human patient, or a subject in need of therapy for an ischemic tissue or a patient exhibiting at least one symptom of tissue ischemia. The amount of stem or progenitor cells contained in the therapeutic composition and administered to a patient will vary with the source of the cells, disease state, age, sex, and weight of the individual, and the ability of the stem and progenitor cells to elicit a desired response in the individual.

1. Dose

Administration of an "amount" of stem and progenitor cells to a subject refers to administration of "an amount effective" to achieve the desired therapeutic or prophylactic result, including without limitation treatment of the subject.

A "therapeutically effective amount" refers to an amount of stem and progenitor cells that is effective to "treat" a subject (e.g., a patient). A therapeutically effective amount is also one in which any toxic or detrimental effects of the hematopoietic stem or progenitor cells are outweighed by the therapeutically beneficial effects.

A "prophylactically effective amount" refers to an amount of stem or progenitor cells effective to achieve the desired prophylactic result. Typically, but not necessarily, since a prophylactic dose is used in subjects prior to or at an earlier stage of disease, the prophylactically effective amount is less than the therapeutically effective amount.

In one embodiment, the amount of stem or progenitor cells (e.g., CD34+ cells) in the composition administered to a subject is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

In one embodiment, the amount of stem or progenitor cells in the composition administered to a subject is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

One of ordinary skill in the art would recognize that multiple administrations of the compositions of the invention may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In preferred embodiments, the stem or progenitor cells are hematopoietic stem and progenitor cells.

2. Formulation

The compositions of the present invention may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation or cell grafts, biomaterials, scaffolds, etc.

In various embodiments, a biocompatible scaffold or graft is provided to promote repair, replacement, and/or regeneration of a damaged, injured, or diseased tissue or organ, e.g., an ischemic tissue.

In certain illustrative embodiments, a method for treating a subject in need of the HSPCs of the invention comprises providing an biocompatible scaffold or cell graft comprising HSPCs of the invention. As used herein, the term "biocompatible scaffold" or "cell graft" refers to a biocompatible natural and/or synthetic structure comprising one or more cell-based compositions, cells, tissues, polymers, polynucleotides, lattices, and/or matrices that is injected, applied to the surface of, or engrafted within a patient or subject that is suitable for directing or attracting a cell-based composition to repair, regenerate, or replace a cell, tissue or organ in vivo.

In particular illustrative embodiments, an implant comprises a biocompatible matrix that can be molded into any suitable form and has especially important roles to prepare tissues in a three-dimensional shape having a certain depth or height or a flat sheet-like shape for application to dermal wounds. Biomaterial science is an established and evolving field (Takayama et al., Principles of Tissue Engineering, Second Edition, edit Lanza R P, Langer R, Vacanti J., Academic Press, San Diego, 2000, pg 209-218; Saltmann et al., Principles of Tissue Engineering, Second Edition, edit Lanza R P, Langer R, Vacanti J., Academic Press, San Diego, 2000, p 221-236; Hubbell et al., Principles of Tissue Engineering, Second Edition, edit Lanza R P, Langer R, Vacanti J., Academic Press, San Diego, 2000, p 237-250; Thomson et al., Principles of Tissue Engineering, Second Edition, edit Lanza R P, Langer R, Vacanti J., Academic Press, San Diego, 2000, p 251-262; Pachence et al., Principles of Tissue Engineering, Second Edition, edit Lanza R P, Langer R, Vacanti J., Academic Press, San Diego, 2000, p 263-278).

Chemists have developed methods to synthesize biocompatible scaffold comprising polymers to direct and modulate cell growth in vitro, ex vivo, and in vivo. The physical properties of the polymers can be modulated to create solid and liquid matrices of specific strengths and viscosities. Some polymers are stable in vivo and will remain in a patient's body for up to 1, 2, 3, 4, 5, 10, 15 or more years. Other polymers are also biodegradable, resorbing at a fixed rate over time to allow replacement by newly synthesized extracellular matrix proteins. Resorption can occur within days to weeks or months following implantation (Pachence et al, Principles of Tissue Engineering, Second Edition, edit Lanza R P, Langer R, Vacanti J., Academic Press, San Diego, 2000, p 263-278).

In other illustrative embodiments, an biocompatible scaffold comprises a bioabsorbable material. A porous carrier is preferably made of one component or a combination of multiple components selected from the group consisting of collagen, collagen derivatives, hyaluronic acid, hyaluronates, chitosan, chitosan derivatives, polyrotaxane, polyrotaxane derivatives, chitin, chitin derivatives, gelatin, fibronectin, heparin, laminin, and calcium alginate; wherein a support member is made of one component or a combination of multiple components selected from the group consisting of polylactic acid, polyglycolic acid, polycaprolactone, polylactic acid-polyglycolic acid copolymer, polylactic acid-polycaprolactone copolymer, and polyglycolic acid-polycaprolactone copolymer (see, for example, U.S. Pat. Nos. 5,077,049 and 5,42,033, and U.S. Patent Application Publication No. 2006/0121085, of which the polymer formulations and methods of making the same of each patent and application is incorporated herein in its entirety).

In particular illustrative embodiments of the present invention, the biocompatible scaffold or cell graft comprises a viscous, biocompatible liquid material. The biocompatible liquid is capable of gelling at body temperature and is selected from the group consisting of alginate, collagen, fibrin, hyaline, or plasma. The viscous, biocompatible liquid material can also be combined with a malleable, three dimensional matrix capable of filling an irregular tissue defect. The matrix is a material including, but not limited to, polyglycolic-polylactic acid, poly-glycolic acid, poly-lactic acid, or suture-like material.

In further illustrative embodiments, biocompatible scaffolds or cell grafts comprising matrices can be molded into desired shapes (e.g., two-dimensional or three-dimensional structures) conducive to or facilitating cell, tissue, and/or organ development. The implant can be formed from polymeric material, having fibers such as a mesh or sponge. Such a structure provides sufficient area on which the cells can grow and proliferate. Desirably, the matrices of the scaffolds or cell grafts are biodegradable over time, so that they will be absorbed into the animal matter as it develops. Suitable polymers can be homopolymers or heteropolymers and can be formed from monomers including, but not limited to glycolic acid, lactic acid, propyl fumarate, caprolactone, and the like. Other suitable polymeric material can include a protein, polysaccharide, polyhydroxy acid, polyorthoester, polyanhydride, polyphosphozene, or a synthetic polymer, particularly a biodegradable polymer, or any combination thereof.

Sheet-like scaffolds and grafts provide reparative, replacement, and/or regenerative therapy for dermal tissues, membranes for tooth root coverage procedures, membranous tissues (e.g., dura mater), flat bones (e.g., skull, breastbone) and the like. Tubular implants and grafts provide reparative, replacement, and/or regenerative therapy for arteries, veins, ureters, urethras, nerves, long bones (e.g., femur, fibula, tibia, humerus, radius, ulna, metacarpals, metatarsals, etc.) and the like. Other three dimensional implants and grafts provide reparative, replacement, and/or regenerative therapy for organ transplants (e.g., liver, lung, skin, heart, pancreas, etc.), bone remodeling or mending of all types of bones, dental implants, or for muscle, tendon, ligament, and cartilage grafts.

In one embodiment, a method for treating or ameliorating an ischemic tissue or tissue damaged by ischemia or at least one symptom associated with an ischemic tissue or a tissue damaged by ischemia, comprises direct administration, to an ischemic tissue, of a biocompatible scaffold or cell graft comprising HSPCs of the invention.

In particular illustrative embodiments of the methods described herein for treating or ameliorating an ischemic tissue or tissue damaged by ischemia or at least one symptom associated with an ischemic tissue or a tissue damaged by ischemia, comprise direct administration, to an ischemic tissue, of a biocompatible scaffold or cell graft comprising HSPCs treated with a combination of one or more agents that includes (i) $PGE_2$, $dmPGE_2$, 15(S)-15-methyl $PGE_2$, 20-ethyl $PGE_2$, or 8-iso-16-cyclohexyl-tetranor $PGE_2$ and (ii) a glucocorticoid. In more particular embodiments, the methods comprises direct administration, to an ischemic tissue, of a biocompatible scaffold or cell graft comprising HSPCs treated with (i) $PGE_2$ or 16,16-dimethyl $PGE_2$ and (ii) medrysone, hydrocortisone, alclometasone, dexamethasone, methylprednisolone, triamcinolone, or alclometasone. In more particular embodiments, the method comprises direct administration, to an ischemic tissue, of a biocompatible scaffold or cell graft comprising HSPCs treated with (i) $PGE_2$ or 16,16-dimethyl $PGE_2$ and (ii) medrysone.

Sterile, therapeutically acceptable compositions suitable for administration to a subject may comprise one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., *Remington: The Science and Practice of Pharmacy*, 21$^{st}$ ed. 2005).

In particular embodiments, the compositions comprising stem and/or progenitor cells comprise a pharmaceutically acceptable cell culture medium. A composition comprising stem and/or progenitor cells of the present invention can be administered separately by enteral or parenteral administration methods or in combination with other suitable compounds to effect the desired treatment goals.

The pharmaceutically acceptable carrier and/or diluent must be of sufficiently high purity and of sufficiently low toxicity to render it suitable for administration to the human subject being treated. It further should maintain or increase the stability of the therapeutic composition. The pharmaceutically acceptable carrier can be liquid or solid and is selected, with the planned manner of administration in mind, to provide for the desired bulk, consistency, etc., when combined with other components of the therapeutic composition of the invention. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the present invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers envisioned by the invention include, but are not limited to, Dulbecco's phosphate buffered saline (PBS), Ringer's solution, 5% dextrose in water (D5W), and normal/physiologic saline (0.9% NaCl).

These pharmaceutically acceptable carriers and/or diluents may be present in amounts sufficient to maintain a pH of the therapeutic composition of between about 3 and about 10. As such, the buffering agent may be as much as about 5% on a weight to weight basis of the total composition. Electrolytes such as, but not limited to, sodium chloride and potassium chloride may also be included in the therapeutic composition.

The pharmaceutically acceptable carrier, diluents, and other components comprising the administration-ready composition of the invention are derived from U.S. Pharmaceutical grade reagents that will permit the composition to be used in clinical regimens. Typically, these finished reagents, including any medium, solution, or other pharmaceutically acceptable carriers and/or diluents, are sterilized in a manner conventional in the art, such as filter sterilized, and are tested for various undesired contaminants, such as mycoplasma, endotoxin, or virus contamination, prior to use. The pharmaceutically acceptable carrier in one embodiment is substantially free of natural proteins of human or animal origin, and suitable for storing the population of cells of the composition, including hematopoietic stem and progenitor cells.

The invention also contemplates, in part, the use of a pharmaceutically acceptable cell culture medium in particular compositions and/or cultures of the present invention. Such compositions are suitable for administration to human subjects. Generally speaking, any medium that supports the maintenance, growth, and/or health of the stem and/or progenitor cells of the invention are suitable for use as a pharmaceutical cell culture medium. In particular embodiments, the pharmaceutically acceptable cell culture medium is a serum-free medium.

The therapeutic composition may comprise serum-free medium suitable for storing the population of cells comprising the composition. Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein.

Illustrative examples of serum-free medium employed in the present invention include, but are not limited to, QBSF- 60 (Quality Biological, Inc.), StemPro-34 (Life Technologies), AIM V (Life Technologies), and X-VIVO 10 (Bio-Whittaker Catalogue).

In various embodiments, the composition of the invention comprises a sterile solution of human serum albumin (HSA), such as 5% HSA, and low molecular weight (LMW) dextran and is substantially free of mycoplasma, endotoxin, and microbial contamination. In particular embodiments, the therapeutic composition contains less than about 10, 5, 4, 3, 2, 1, 0.1, 0.05 µg/ml bovine serum albumin.

One having ordinary skill in the art would appreciate that the above example of medium is illustrative and in no way limits the formulation of media suitable for use in the present invention and that there are many such media known and available to those in the art.

G. Methods of Treatment

The present invention contemplates, in part, methods of cell-based therapy for treating ischemic tissue or treating or ameliorating one or more symptoms associated with tissue ischemia, including, but not limited to, cramping, claudication, numbness, tingling, weakness, pain, reduced wound healing, inflammation, skin discoloration, and gangrene.

Ischemic tissue may be treated by increased homing of stem and/or progenitor cells to sites of ischemic tissue damage, increased recruitment of endogenous stem cells and endothelial progenitor cells at the ischemic tissue site, increased vascularization at the ischemic tissue site, reducing ischemic tissue necrosis or programmed cell death, or increasing cell survival at the ischemic tissue site. Accordingly, the present invention contemplates, in part, cells having these therapeutic properties would be useful in treating ischemic tissue or a tissue damaged by ischemia or treating or ameliorating at least one symptom associated with an ischemic tissue.

The present inventors have developed stem and progenitor cells that have surprisingly high levels of CXCR4 expression by contacting them with a prostaglandin pathway agonist, and optionally a glucocorticoid. These novel cells can be identified using particular gene expression signatures or by functional assays, e.g., transwell migration assays. The inventors have also determined that these novel cells have therapeutic properties that would be useful in treating ischemic tissue.

Without wishing to be bound to any particular theory, the present invention contemplates, in part, that contacting stem or progenitor cells, e.g., hematopoietic stem or progenitor cells, with a prostaglandin pathway agonist, and optionally a glucocorticoid, under conditions sufficient to increase CXCR4 expression in the contacted stem or progenitor cells to the levels disclosed herein, and to levels not reported in therapeutic cells existing in the art, imbues the contacted stem and progenitor cells with increased therapeutic properties that are useful in treating or ameliorating an ischemic tissue injury or a symptom associated with an ischemic tissue injury.

In various embodiments, the present invention provides a method of treating an ischemic tissue or a tissue damaged by ischemia or at least one symptom associated therewith, comprising administering to a subject a therapeutically effective amount of a composition comprising stem or progenitor cells contacted with a prostaglandin pathway agonist, and optionally a glucocorticoid, and having increased CXCR4 expression, compared to control, vehicle, or non-treated cells. In one embodiment, the cells provide therapy to the subject by increased homing of stem and/or progenitor cells to sites of ischemic tissue damage, increased recruitment of endogenous stem cells and endothelial progenitor cells at the ischemic tissue site, increased stimulation of vascularization at the ischemic tissue site, reducing ischemic tissue necrosis or programmed cell death, or increasing cell survival at the ischemic tissue site.

In various other embodiments, the present invention provides a method of treating or ameliorating an ischemic tissue injury comprising administering to a subject a therapeutically effective amount of a composition comprising hematopoietic stem or progenitor cells contacted with a prostaglandin pathway agonist, and optionally a glucocorticoid, and having increased therapeutic properties, e.g., CXCR4 expression, compared to control, vehicle, or non-treated cells. In one embodiment, the hematopoietic stem or progenitor cells provide therapy to the subject by increased homing of hematopoietic stem and/or progenitor cells to sites of ischemic tissue damage, increased recruitment of endogenous stem cells and endothelial progenitor cells at the ischemic tissue site, increased stimulation of vascularization at the ischemic tissue site, reducing ischemic tissue necrosis or programmed cell death, or increasing cell survival at the ischemic tissue site.

In various other embodiments, the present invention provides a method of treating or ameliorating a symptom associated with an ischemic tissue injury comprising administering to a subject, a therapeutically effective amount of a composition comprising stem or progenitor cells contacted with a $PGE_2$ or $dmPGE_2$, and optionally a glucocorticoid, e.g., medrysone, and having increased therapeutic properties, e.g., CXCR4 expression, compared to control, vehicle, or non-treated cells. In one embodiment, the cells provide therapy to the subject by increased homing of stem and/or progenitor cells to sites of ischemic tissue damage, increased recruitment of endogenous stem cells and endothelial progenitor cells at the ischemic tissue site, increased stimulation of vascularization at the ischemic tissue site, reducing ischemic tissue necrosis or programmed cell death, or increasing cell survival at the ischemic tissue site.

In yet various other embodiments, the present invention provides a method of treating or ameliorating a symptom associated with an ischemic tissue injury comprising administering to a subject, a therapeutically effective amount of a composition comprising hematopoietic stem or progenitor cells contacted with a $PGE_2$ or $dmPGE_2$, and optionally a glucocorticoid, e.g., medrysone, and having increased therapeutic properties, e.g., CXCR4 expression, compared to control, vehicle, or non-treated cells. In one embodiment, the hematopoietic stem or progenitor cells provide therapy to the subject by increased homing of hematopoietic stem or progenitor cells to sites of ischemic tissue damage, increased recruitment of endogenous stem cells and endothelial progenitor cells at the ischemic tissue site, increased stimulation of vascularization at the ischemic tissue site, reducing ischemic tissue necrosis or programmed cell death, or increasing cell survival at the ischemic tissue site.

The methods of the invention are suitable for treating ischemic damage to any type of tissue or a symptom of ischemia associated with any type of tissue. In addition, the methods of the present invention are suitable to treat either focal and global ischemias and ischemias that are acute or chronic or any suitable combinations thereof.

Illustrative examples of tissues that are suitable for treatment with the compositions of the present invention include, mesodermal tissue, endodermal tissue, or ectodermal tissue. Other tissues suitable for treatment with the compositions of the present invention include, but are not limited to, skin tissue, skeletal muscle tissue, cardiac muscle tissue, smooth muscle tissue, cartilage tissue, tendon tissue, bone tissue, brain tissue, spinal cord tissue, retinal tissue, corneal tissue, lung tissue, liver tissue, kidney tissue, pancreatic tissue, ovarian tissue, testicular tissue, intestinal tissue, stomach tissue, and bladder tissue.

In particular embodiments, any tissue that has a compromised blood supply and is ischemic or at risk for becoming ischemic may be treated using the methods of the invention.

The methods of the invention are also suitable for treating ischemic organs or a symptom associated with an ischemic organ. Illustrative examples of organs that are suitable for treatment with the compositions of the present invention include, but are not limited to, skin, bone, heart, brain, spinal cord, eye, lung, liver, gall bladder, kidney, pancreas, ovary, testes, intestine, stomach, and bladder.

In various embodiments, the methods of the invention are suitable for treating ischemia that results from or is associated with any genetic disorder, syndromic condition, traumatic injury, chronic condition, medical intervention, or any other cause of ischemia known to those having ordinary skill in the art.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for treatment or amelioration using the methods of the present invention, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease (thromboangiitis obliterans), burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present invention, include, ischemia resulting from surgery, chemotherapy, radiation therapy, or cell, tissue, or organ transplant or graft.

In various embodiments, the methods of the present invention are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, the present invention contemplates that the therapeutic cell compositions disclosed herein can be used to treat an ischemic tissue in which it is desirable to increase the blood flow, oxygen supply, glucose supply, or supply of nutrients to the tissue.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

SDF-1 Transwell Migration Assays

Methods

Transwell migration assays were performed using 96-well chemotaxis chambers, 5 µM pore size polycarbonate membrane (Corning Inc., Corning, N.Y.) in accordance with manufacturer's instructions. Briefly, CD34$^+$ cells were then treated for 4 hours at 37° C. with 16,16-dimethyl $PGE_2$ ($dmPGE_2$), $dmPGE_2$ and glucocorticoid, or DMSO control at a concentration of 10 µM in StemSpan® media (StemCell Technology, Vancouver, Canada). The cells were then washed by centrifugation (300 g for 10 minutes) and resuspended in transwell assay buffer (Phenol Red Free RPMI media (Mediatech), 0.5% lipid free BSA (Sigma-Aldrich) at a concentration of 40,000-60,000 cells/75 µl.

To test the duration of the treatment effects, one portion of treated cells was washed by centrifugation (300 g for 10 minutes) and resuspended in StemSpan® media for 4 hours at 37° C. without $dmPGE_2$, glucocorticoids, or DMSO and then washed again by centrifugation (300 g for 10 minutes) and resuspended in transwell assay buffer (Phenol Red Free RPMI media (Mediatech), 0.5% lipid free BSA (Sigma-Aldrich) at a concentration of 40,000-60,000 cells/75 µl.

Seventy-five µl of cell suspension was added to the upper chamber of the plate, while 235 µl of transwell assay media containing 0 or 50 ng/ml SDF 1α (R&D system, Minneapolis, Minn.) was added to the bottom well. Total cell number in the lower well was obtained by flow cytometry after 2.5 hours of incubation at 37° C., 5% $CO_2$.

Results $CD34^+$ cells were treated with DMSO control, $dmPGE_2$, or $dmPGE_2$ and medrysone as described above. The treated cells were placed in the upper chambers of a transwell culture plate with 0 ng/mL SDF1 or 50 ng/mL SDF1 in the lower chambers. Migration was expressed as the % of cells added, i.e., the number of cells in the lower chamber normalized to the number of cells initially added to the upper chamber. $dmPGE_2$ treatment increased SDF1-driven migration compared to the DMSO control (See FIG. 1). The combination treatment of $dmPGE_2$ and medrysone increased SDF1-driven cell migration more than $dmPGE_2$ alone or DMSO control (See FIG. 1). Thus, $CD34^+$ cells treated with $dmPGE_2$, or $dmPGE_2$ and medrysone migrated more efficiently towards SDF1 compared to DMSO control treated cells.

Figure 2:
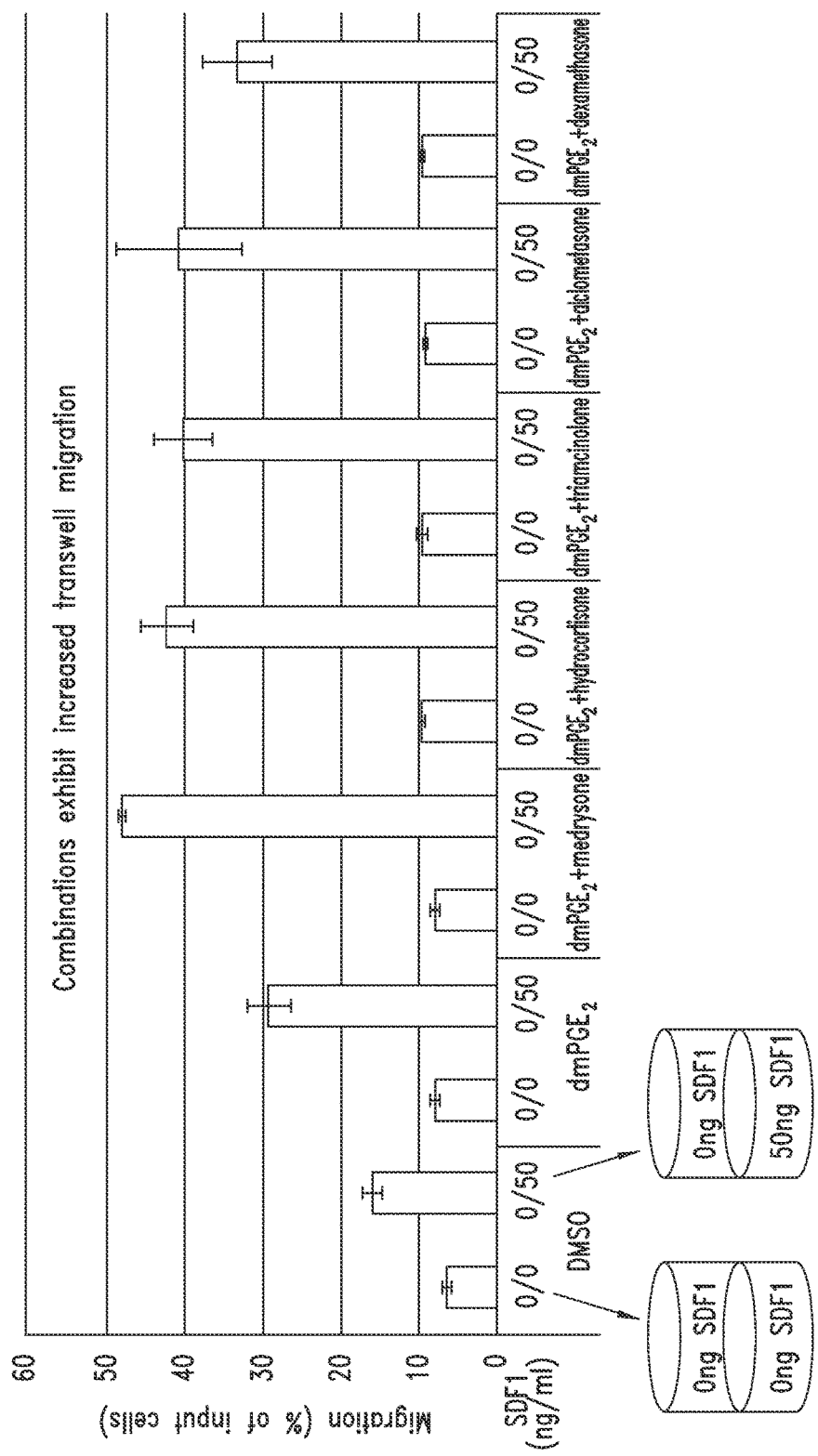
FIG. 2 shows the results from a representative SDF1 transwell migration assay. The results show the effect of treating CD34$^+$ cells with DMSO control, dmPGE$_2$, or dmPGE$_2$ and various glucocorticoids on the efficiency of cell migration towards SDF 1.

$CD34^+$ cells were treated with DMSO control, $dmPGE_2$, or $dmPGE_2$ and a glucocorticoid (medrysone, hydrocortisone, triamcinolone, alclometasone, alclometasone dipropionate, or dexamethasone) as described above. The treated cells were placed in the upper chambers of a transwell culture plate with 0 ng/mL SDF1 or 50 ng/mL SDF1 in the lower chambers. Migration was expressed as the % of cells added, i.e., the number of cells in the lower chamber normalized to the number of cells initially added to the upper chamber. $dmPGE_2$ treatment increased SDF1-driven cell migration compared to the DMSO control (See FIG. 2). Moreover, treatment with dmPGE2 combined with either medrysone, hydrocortisone, triamcinolone, alclometasone, alclometasone dipropionate, or dexamethasone increased SDF 1-driven cell migration more effectively than dmPGE2 alone or DMSO control (See FIG. 2). Thus, $CD34^+$ cells treated with $dmPGE_2$, or $dmPGE_2$ and various glucocorticoids migrated more efficiently towards SDF1 compared to DMSO control treated cells and showed that the enhanced migration property of the prostaglandin pathway agonist/glucocorticoid treated cells is not limited to a particular glucocorticoid.

Figure 3:
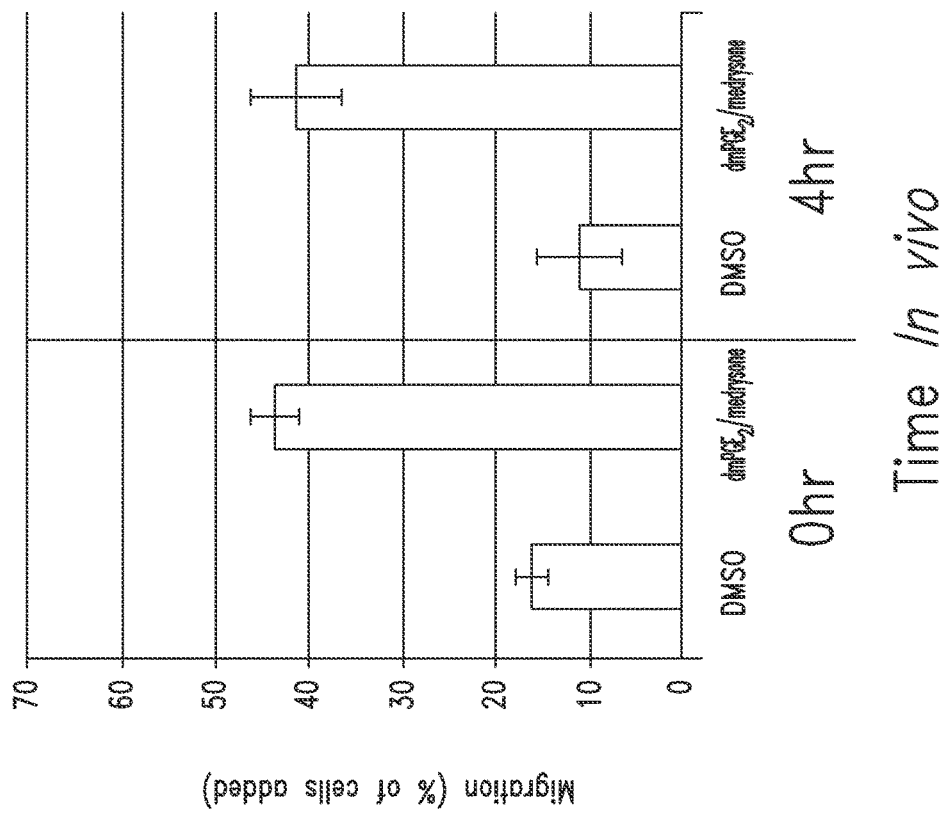
FIG. 3 shows the results from a representative SDF1 transwell migration assay. The results show the duration of the enhanced migration effect by dmPGE$_2$ and medrysone on cell migration towards SDF 1.
Figure 3:
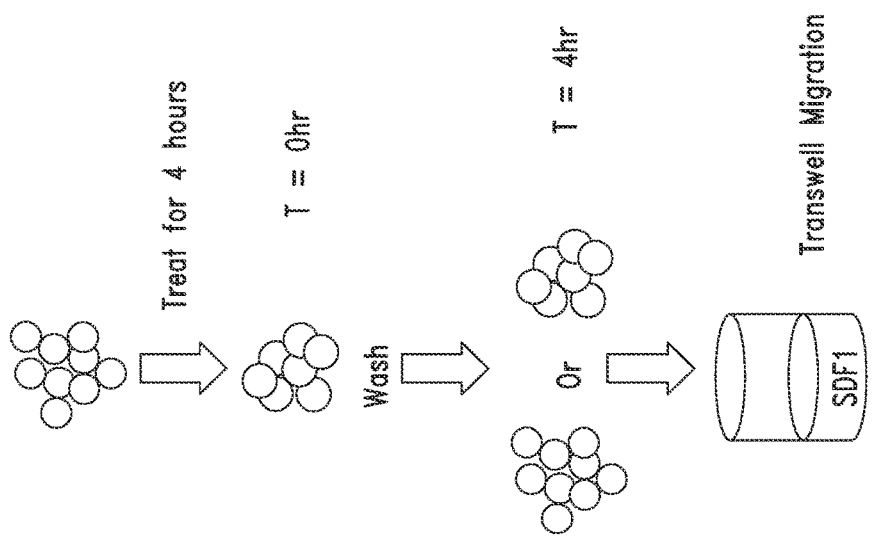

The duration of the enhanced migration effect of $dmPGE_2$/glucocorticoid treated cells towards SDF1 was tested. $CD34^+$ cells were treated with DMSO or $dmPGE_2$ and medrysone. Freshly treated cells or treated cells incubated for an additional 4 without further treatment (as described above) were placed in the upper chambers of a transwell culture plate with 0 ng/mL SDF1 or 50 ng/mL SDF1 in the lower chambers. Migration was expressed as the % of cells added, i.e., the number of cells in the lower chamber normalized to the number of cells initially added to the upper chamber. $dmPGE_2$ and medrysone treatment increased SDF1-driven cell migration compared to the DMSO control (See FIG. 3). Moreover, $dmPGE_2$ and medrysone treated cells incubated for an additional 4 hours with no further treatment migrated as well as the freshly treated cells. Thus, the enhanced migration effect of prostaglandin pathway agonist/glucocorticoid treated cells towards SDF1 is stable for at least four hours, an indicated that the effect would also be present in administering the treated cells to a subject.

Example 2

$PGE_2$ and $PGE_2$/Glucocorticoid Treated HSPCs Improve Neurological and Locomotor Function in a Rat Ischemia Model Methods Adult male Wistar rats were subjected to a transient focal ischemia by blocking the right middle cerebral artery MCAO model (Middle Cerebral Artery Occlusion). A surgical nylon suture with a rounded tip was advanced from the external carotid artery into the lumen of the internal carotid artery until it blocked the origin of the middle cerebral artery. After 2 hours, the suture was withdrawn to allow reperfusion. One day after reperfusion, rats were injected via tail vein with either Hanks Balanced Salt Solution (HBSS), DMSO-treated HSPCs, or HSPCs treated with $dmPGE_2$ and medrysone. A phosphodiesterase type 4 inhibitor (YM976) was also included to increase the durability of the enhanced cell effect. Our work demonstrates that PDE4 inhibitors do not significantly change the properties of the enhanced cell. Cells were incubated with compound or DMSO in culture medium for 4 hours at 37° C. Before injection, pretreated cells were centrifuged; the resultant supernatant was aspirated; and the cell pellet was resuspended in HBSS.

One day and 1, 2, 3, 4 and 5 weeks after injection, rats were assessed for neurological deficits with behavioral testing performed by an investigator who was blinded to the experimental groups. A modified Neurological Severity Score (mNSS) was calculated based on a published panel of motor, sensory, balance and reflex tests (Chen et al., Stroke 32:2682-2688 (2001)).

In addition, 1 day and 1, 2, 3, 4 and 5 weeks after injection, locomotor function was evaluated in the treated rats with a foot-fault test in which the animal crossed a perforated walkway. The total number of forelimb steps and the number of missteps, in which the left forelimb fell through a perforation, were measured.

Results

Figure 4:
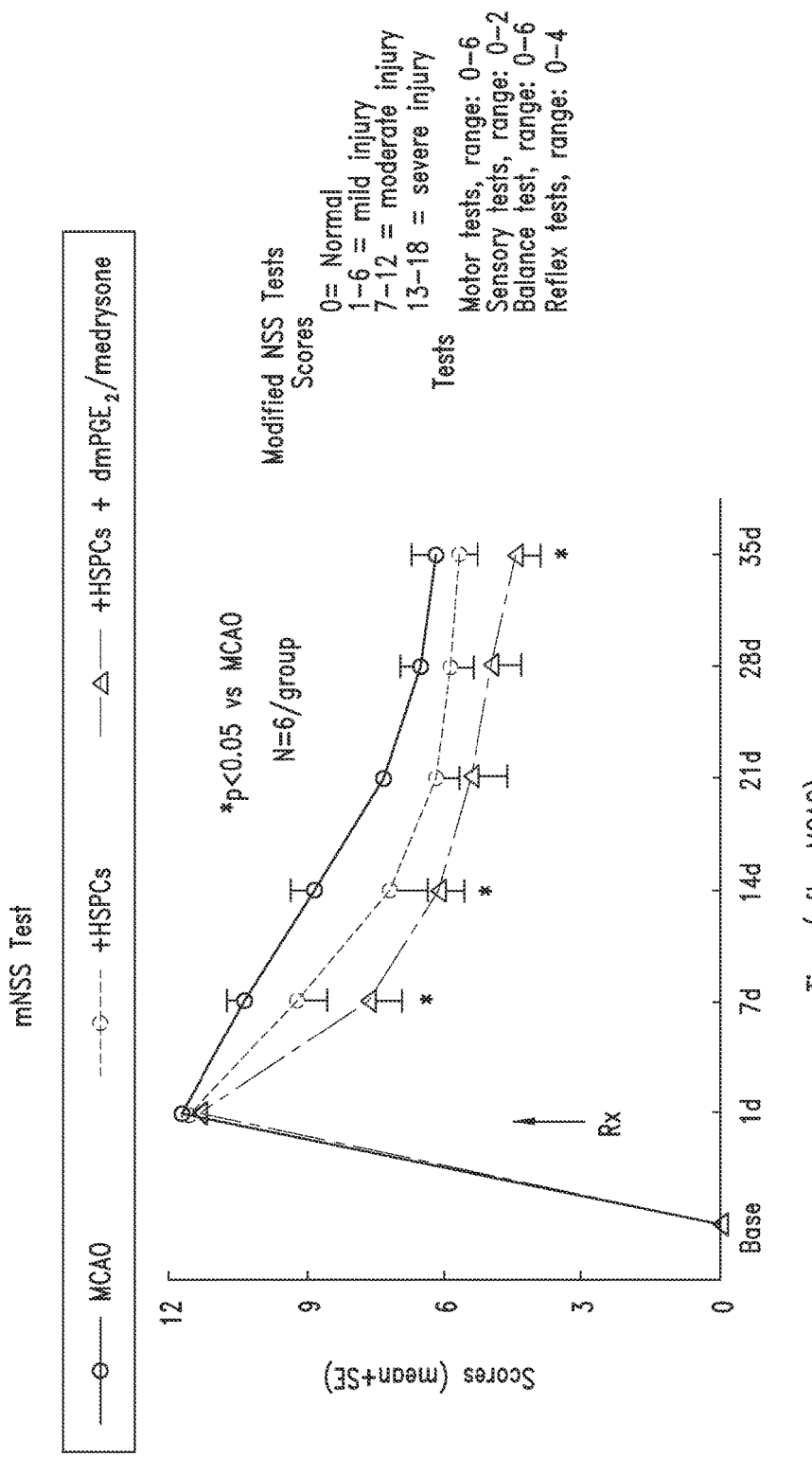
FIG. 4 shows the Neurological Severity Score (mNSS) results from a representative middle cerebral artery occlusion model (MCAO) ischemia rat model. The results show the effect of treating HSPCs with dmPGE$_2$ and medrysone on the ability of the cells to reduce neurological deficits in the MCAO stroke model.

Rats were administered treated HSPCs, and the ability of the treatment effect to reduce neurological deficit in the MCAO stroke model was tested. Treated HSPCs were intravenously injected 24 hours after unilateral ischemic brain injury. Neurological function was assessed with a battery of behavioral tests and reported as mNSS. Cells treated with $dmPGE_2$ and medrysone significantly improved mNSS at 7, 14 and 35 days compared to vehicle control, while DMSO-treated cells did not significantly affect mNSS (See FIG. 4). *$p<0.05$ (n=6/group).

Figure 5:
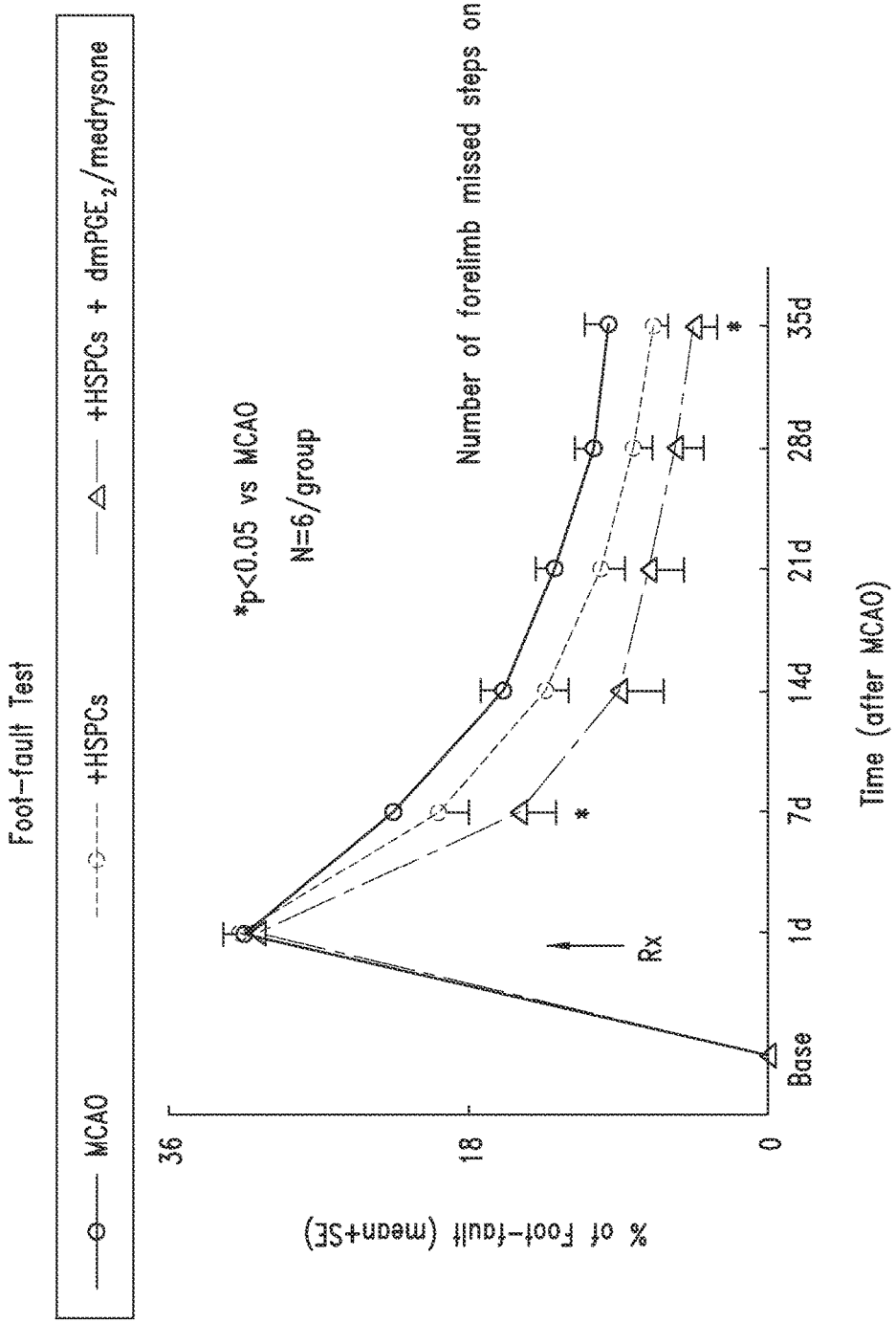
FIG. 5 shows the foot-fault assay results from a representative middle cerebral artery occlusion model (MCAO) ischemia rat model. The results show the effect of treating HSPCs with dmPGE$_2$ and medrysone on the ability of the cells to reduce locomotor deficits in the MCAO stroke model.

Rats were administered HSPCs treated with $dmPGE_2$ and medrysone, and the ability of the treatment effect to reduce locomotor deficit in the MCAO stroke model was tested. Treated HSPCs were intravenously injected 24 hours after unilateral ischemic brain injury. Locomotor function was assessed as % foot-faults when crossing a perforated walkway. Cells treated with $dmPGE_2$ and medrysone significantly decreased % foot-faults at 7 and 35 days compared to vehicle control, while DMSO-treated cells did not significantly affect % foot-faults (See FIG. 5). *$p<0.05$ (n=6/group).

Thus, the HSPCs treated with a prostaglandin pathway antagonist and a glucocorticoid effectively treated ischemia and the symptoms associated therewith, in the rat MCAO model.

Example 3

Methods

Isolation of Lin(−)CD34+ Cells from Treated Whole Cord Blood

Human whole cord blood mononuclear cells were obtained from Stem Cell Technologies (Vancouver, Canada). Upon thawing, the cells were treated with 16,16-dimethyl PGE$_2$ or appropriate controls, e.g., DMSO, in LMD/5% HSA medium.

After treatment, the cells were washed with LMD/5% HSA medium, centrifuged for 10 minutes at 650×g at room temperature and resuspended in a cold selection buffer (phosphate buffered saline (PBS) with no Ca$^+$ or Mg$^+$; 2 mM EDTA; and 0.5% HSA). Magnetic selection was performed using the Lineage (Lin) Depletion Kit (Miltenyi Biotec, CA) followed by a CD34$^+$ enrichment kit (Miltenyi Biotec). Lineage depletion and CD34$^+$ cell enrichment were performed according to manufacturer's instructions using a QuadroMACS™ separator. During this process, the cells were kept at 4° C. Once the Lin-CD34$^+$ cells were isolated from the treated whole cord blood, an aliquot was analyzed by flow cytometry to assess purity. Purity of the cells was greater than 90%. The majority of the cells were used for RNA extraction using the Pico Pure RNA Isolation Kit (Molecular Devices, Sunnyvale, Calif.) for Affymetrix analysis.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method of increasing stem or progenitor cell homing to an ischemic tissue or a tissue damaged by ischemia, comprising:
    (a) treating stem or progenitor cells ex vivo with a prostaglandin pathway agonist and a glucocorticoid; and
    (b) administering a composition comprising the treated stem or progenitor cells to a subject having an ischemic tissue or a tissue damaged by ischemia.

2. A method of treating a subject having an ischemic tissue or a tissue damaged by ischemia comprising: administering a therapeutically effective amount of a composition comprising stem or progenitor cells treated ex vivo with a prostaglandin pathway agonist and a glucocorticoid.

3. A method of ameliorating at least one symptom associated with an ischemic tissue or a tissue damaged by ischemia in a subject comprising: administering a therapeutically effective amount of a composition comprising stem or progenitor cells treated ex vivo with a prostaglandin pathway agonist and a glucocorticoid.

4. The method according to any one of claims 1 to 3, wherein the treatment of the stem or progenitor cells is sufficient to increase the percent (%) migration in an SDF-1 transwell migration assay at least two fold in the treated stem or progenitor cells compared to non-treated stem or progenitor cells.

5. The method of any one of claims 1 to 3, wherein:
    a) the stem or progenitor cells have been treated at a temperature of about 22° C. to about 37° C. for a period of time of less than about 24 hours;
    b) the stem or progenitor cells have been treated at a temperature of about 22° C. to about 37° C. for a time of about one to about four hours; or
    c) the stem or progenitor cells have been treated at a temperature of about 37° C. for a time of about 4 hours.

6. The method of any one of claims 1 to 3, wherein:
    a) the stem or progenitor cells are embryonic stem cells;
    b) the stem or progenitor cells are adult stem cells;
    c) the stem or progenitor cells are selected from the group consisting of: endothelial stem or progenitor cells, mesodermal stem or progenitor cells, and ectodermal stem or progenitor cells;
    d) the stem or progenitor cells are selected from the group consisting of: mesenchymal stem or progenitor cells, hematopoietic stem or progenitor cells, placental stem or progenitor cells, umbilical cord stem or progenitor cells, bone marrow stem cells, and Wharton's jelly stem or progenitor cells;
    e) the stem or progenitor cells are hematopoietic stem or progenitor cells;
    f) the stem or progenitor cells are isolated from peripheral blood, bone marrow, umbilical cord blood, Wharton's jelly, placenta, or fetal blood;
    g) the stem or progenitor cells are CD34+ cells;
    h) the stem or progenitor cells are, or have been, expanded ex vivo prior to the treatment of the cells;
    i) the stem or progenitor cells are allogeneic or autologous;
    j) the stem or progenitor cells are allogeneic and have a complete or partial HLA-match with the patient;
    k) the stem or progenitor cells are not matched with the patient;
    l) the stem or progenitor cells are xenogeneic; or
    m) the stem or progenitor cells are washed to substantially remove the prostaglandin pathway agonist or glucocorticoid in the composition, prior to administration of the composition to the subject.

7. The method of any one of claims 1 to 3, wherein:
    a) the prostaglandin pathway agonist is selected from the group consisting of: a prostaglandin, a prostaglandin EP2 receptor agonist, a prostaglandin EP4 receptor agonist and an agent having 16,16-dimethyl PGE2 (dmPGE2) activity;
    b) the prostaglandin pathway agonist is selected from the group consisting of: prostaglandin E$_2$ (PGE$_2$), and dmPGE$_2$;
    c) the glucocorticoid is selected from the group consisting of: alclometasone, alclometasone dipropionate, amcinonide, beclometasone, beclometasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, medrysone, meprednisone, 6a-methylprednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol;
d) the glucocorticoid is selected from the group consisting of: medrysone, hydrocortisone, alclometasone, dexamethasone, methylprednisolone, triamcinolone or Cortisol; or
e) the prostaglandin pathway agonist is $PGE_2$ or $dmPGE_2$ or an analogue thereof, and the glucocorticoid is medrysone or dexamethasone.

8. The method of any one of claims 1 to 3, wherein:
a) expression of one or more genes associated with increased homing of the stem or progenitor cells to the ischemic tissue or tissue damaged by ischemia, is increased at least two fold in the treated stem or progenitor cells compared to non-treated stem or progenitor cells, wherein the one or more genes is selected from the group consisting of: CXCR4, hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), and Fos-related antigen 2 (FOSL2);
b) the gene expression of at least one of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells;
c) the gene expression of at least one of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells;
d) the gene expression of at least one of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells;
e) the gene expression of at least one of HAS1, GEM, DUSP4, AREG, NR4A2, REN, CREM, COL1A1, FOSL2, and CXCR4 is increased by at least about fifty fold in the treated stem or progenitor cells compared to non-treated stem or progenitor cells;
f) the gene expression of at least one of HAS1, GEM, DUSP4, AREG, NR4A2, REN, CREM, COL1A1, FOSL2, and CXCR4 is increased by at least about sixty fold in the treated stem or progenitor cells compared to non-treated stem or progenitor cells;
g) the gene expression of at least one of HAS1, GEM, DUSP4, AREG, NR4A2, REN, CREM, COL1A1, FOSL2, and CXCR4 is increased by at least about seventy fold in the treated stem or progenitor cells compared to non-treated stem or progenitor cells;
h) the gene expression of at least one of HAS1, GEM, DUSP4, AREG, NR4A2, REN, CREM, COL1A1, FOSL2, and CXCR4 is increased by at least about eighty fold in the treated stem or progenitor cells compared to non-treated stem or progenitor cells;
i) the gene expression of at least two of HAS1, GEM, DUSP4, AREG, NR4A2, REN, CREM, COL1A1, FOSL2, and CXCR4 is increased by at least about two fold in the treated stem or progenitor cells compared to non-treated stem or progenitor cells;
j) the gene expression of at least two of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells;
k) the gene expression of at least two of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells;
l) the gene expression of at least two of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells;
m) the gene expression of at least three of HAS1, GEM, DUSP4, AREG, NR4A2, REN, CREM, COL1A1, FOSL2, and CXCR4 is increased by at least about two fold in the treated stem or progenitor cells compared to non-treated stem or progenitor cells;
n) the gene expression of at least three of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells;
o) the gene expression of at least three of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells;
p) the gene expression of at least three of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells;
q) the gene expression of at least five of HAS1, GEM, DUSP4, AREG, NR4A2, REN, CREM, COL1A1, FOSL2, and CXCR4 is increased by at least about two fold in the treated stem or progenitor cells compared to non-treated stem or progenitor cells;
r) the gene expression of at least five of HAS1, GEM, DUSP4, AREG, NR4A2, REN, CREM, COL1A1, FOSL2, and CXCR4 is increased by at least about five fold in the treated stem or progenitor cells compared to non-treated stem or progenitor cells;
s) the gene expression of at least five of HAS1, GEM, DUSP4, AREG, NR4A2, REN, CREM, COL1A1, FOSL2, and CXCR4 is increased by at least about ten fold in the treated stem or progenitor cells compared to non-treated stem or progenitor cells; or
t) the gene expression of at least five of HAS1, GEM, DUSP4, AREG, NR4A2, REN, CREM, COL1A1, FOSL2, and CXCR4 is increased by at least about twenty fold in the treated stem or progenitor cells compared to non-treated stem or progenitor cells.

9. The method of claim 4, wherein:
a) the % migration of the treated cells in an SDF-1 transwell migration assay is increased at least three fold in the treated stem or progenitor cells compared to non-treated stem or progenitor cells;
b) the % migration of the treated cells in an SDF-1 transwell migration assay is increased at least three fold in the treated stem or progenitor cells compared to non-treated stem or progenitor cells;

c) the % migration of the treated cells in an SDF-1 transwell migration assay is increased at least four fold in the treated stem or progenitor cells compared to non-treated stem or progenitor cells d) the % migration of the treated cells in an SDF-1 transwell migration assay is increased at least five fold in the treated stem or progenitor cells compared to non-treated stem or progenitor cells;

e) the % migration of the treated cells in an SDF-1 transwell migration assay is increased at least ten fold in the treated stem or progenitor cells compared to non-treated stem or progenitor cells; or f) the % migration of the treated cells in an SDF-1 transwell migration assay is increased at least twenty fold in the treated stem or progenitor cells compared to non-treated stem or progenitor cells.

10. The method of any one of claims 1 to 3, wherein:

a) the ischemia is associated with acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, frostbite, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, or wounds to tissues or organs;

b) the subject has cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia;

c) the subject has had surgery, chemotherapy, radiation therapy, or a cell, tissue, or organ transplant;

d) the ischemic tissue or tissue damaged by ischemia is selected from the group consisting of: skin tissue, skeletal muscle tissue, cardiac muscle tissue, smooth muscle tissue, cartilage tissue, tendon tissue, brain tissue, spinal cord tissue, retinal tissue, corneal tissue, lung tissue, liver tissue, kidney tissue, pancreatic tissue, ovary tissue, testes tissue, intestinal tissue, stomach tissue, and bladder tissue;

e) the ischemic tissue or tissue damaged by ischemia has decreased blood flow, hypoxia, anoxia, hypoglycemia, decreased metabolism, increased necrosis, or increased apoptosis compared to non-ischemic tissue; or f) the one or more symptoms associated with the ischemic tissue or tissue damaged by ischemia is selected from the group consisting of: cramping, claudication, numbness, tingling, weakness, pain, reduced wound healing, inflammation, skin discoloration, and gangrene.

11. The method of any one of claims 1 to 3, wherein:

a) the composition comprises hematopoietic stem or progenitor cells, the prostaglandin pathway agonist is 16,16-dmPGE$_2$ or PGE$_2$, the gene expression of CXCR4 is increased by at least five fold in the treated cells compared to non-treated cells, and the hematopoietic stem or progenitor cells have been contacted with 16,16-dmPGE$_2$ at a temperature of about 37° C. for a time of about two hours; or b) the composition comprises hematopoietic stem or progenitor cells, the prostaglandin pathway agonist is 16,16-dmPGE$_2$ or PGE$_2$, the glucocorticoid is selected from the group consisting of medrysone, hydrocortisone, alclometasone, dexamethasone, methylprednisolone, triamcinolone or Cortisol, the gene expression of CXCR4 is increased by at least five fold in the treated cells compared to non-treated cells, and wherein the hematopoietic stem or progenitor cells have been contacted with 16,16-dmPGE$_2$ at a temperature of about 37° C. for a time of about two hours.

12. The method of any one of claims 1 to 3 wherein the prostaglandin pathway agonist is 16,16-dmPGE2 or PGE2 and the glucocorticoid is dexamethasone.

\* \* \* \* \*